United States Patent
Sauer et al.

(10) Patent No.: US 8,926,640 B2
(45) Date of Patent: Jan. 6, 2015

(54) METHOD AND APPARATUS FOR CLOSING AN OPENING IN THICK, MOVING TISSUE

(75) Inventors: Jude S. Sauer, Pittsford, NY (US); Mark A. Bovard, Mendon, NY (US); John F. Hammond, Canandaigua, NY (US)

(73) Assignee: LSI Solutions, Inc., Victor, NY (US)

( * ) Notice: Subject to any disclaimer, the term of this patent is extended or adjusted under 35 U.S.C. 154(b) by 620 days.

(21) Appl. No.: 12/835,464

(22) Filed: Jul. 13, 2010

(65) Prior Publication Data
US 2012/0016383 A1 Jan. 19, 2012

(51) Int. Cl.
*A61B 17/04* (2006.01)
*A61B 17/00* (2006.01)
*A61B 17/02* (2006.01)

(52) U.S. Cl.
CPC ......... *A61B 17/0483* (2013.01); *A61B 17/0057* (2013.01); *A61B 17/0469* (2013.01); *A61B 2017/00557* (2013.01); *A61B 2017/00663* (2013.01); *A61B 2017/00986* (2013.01); *A61B 2017/0243* (2013.01); *A61B 2017/0404* (2013.01); *A61B 2017/0472* (2013.01)
USPC ............ 606/145; 606/144; 606/148

(58) Field of Classification Search
None
See application file for complete search history.

(56) References Cited

U.S. PATENT DOCUMENTS

| | | | |
|---|---|---|---|
| 4,852,568 A | 8/1989 | Kensey | |
| 4,929,240 A | 5/1990 | Kirsch et al. | |
| 5,342,393 A | 8/1994 | Stack | |
| 5,368,611 A | 11/1994 | Owenby et al. | |
| 5,431,666 A | 7/1995 | Sauer et al. | |
| 5,620,456 A | 4/1997 | Sauer et al. | |
| 5,766,183 A | 6/1998 | Sauer | |
| 5,891,159 A * | 4/1999 | Sherman et al. | 606/144 |
| 6,368,334 B1 | 4/2002 | Sauer | |
| 6,533,795 B1 * | 3/2003 | Tran et al. | 606/144 |
| 6,641,592 B1 | 11/2003 | Sauer et al. | |
| 6,770,084 B1 * | 8/2004 | Bain et al. | 606/144 |
| 6,978,176 B2 | 12/2005 | Lattouf | |
| 6,997,931 B2 | 2/2006 | Sauer et al. | |
| 7,407,505 B2 | 8/2008 | Sauer et al. | |

(Continued)

FOREIGN PATENT DOCUMENTS

EP 0669101 A1 8/1995

OTHER PUBLICATIONS

American Association of Thoracic Surgeons (May 2010) Relevant pp. 82,83;100-103; and 174,175.

(Continued)

*Primary Examiner* — Melanie Tyson
*Assistant Examiner* — Todd J Scherbel

(57) ABSTRACT

A device for placing sutures through thick and/or moving tissue such as the wall of a beating heart. The device includes a tissue welting tip having a trough for forming a welt in a tissue section, an alignment guide having an opening receiving a guide wire and pivotally mounted in the distal end adjacent to the trough, and an elongated sleeve slidably engagable with the guide wire. The device also includes one or more expandable tissue engaging member(s) on the sleeve expandable from a collapsed configuration having a diameter small enough to pass through the opening in the tip to an expanded configuration having a diameter large enough to engage a tissue section and urge it into the trough to form a welt in the tissue section and a retractable needle extendable through at least two portions of a tissue section while the tissue section is engaged with the trough.

34 Claims, 22 Drawing Sheets

(56) References Cited

U.S. PATENT DOCUMENTS

| | | | |
|---|---|---|---|
| 7,635,386 | B1 | 12/2009 | Gammie |
| 7,731,727 | B2 | 6/2010 | Sauer |
| 8,469,974 | B2* | 6/2013 | Skinlo et al. .................. 606/144 |
| 2003/0120289 | A1* | 6/2003 | McGuckin et al. ........... 606/151 |
| 2004/0068272 | A1 | 4/2004 | Sauer et al. |
| 2005/0165419 | A1 | 7/2005 | Sauer et al. |
| 2007/0255296 | A1 | 11/2007 | Sauer |
| 2007/0270793 | A1 | 11/2007 | Lattouf |
| 2009/0306685 | A1* | 12/2009 | Fill ............................... 606/148 |
| 2011/0238090 | A1* | 9/2011 | Heneveld ...................... 606/144 |

OTHER PUBLICATIONS

Battellini et al.: "Transapical Aortic Valve Implantation", Cardiovascular Surgery/Valvular Heart Diseases (Jun. 19, 2008) (5 pages), Revista Argentina De Cardiologia vol. 77, No. 2 (Mar.-Apr. 2009), Germany.

"Edwards Unveils Ascendra Aortic Heart Valve Replacement System", Edwards Lifesciences (Nov. 29, 2005) (1 page), http://www.edwards.com, Irvine, CA.

Filmore: "Medtronic Catapults Into Transcatheter Valve Market With Billion-Dollar Buys", Medical Devices Today (Mar. 2, 2009) (3 pages), http://www.medicaldevicestoday.com.

"Transapical Implantation of Ventor Embracer™ Valve in Patients With Severe Aortic Valve Disease", Ventor Technologies, ClinicalTrials.gov (May 12, 2008) (4 pages).

Dooren, "Medtronic Valve Wins FDA Approval", The Wall Street Journal (Jan. 26, 2010) (2 pages) http://online.wsj.com.

Miller: "St. Jude Unveils Plan to Launch Transcatheter Aortic Valve by 2012", Medical Devices Today (Feb. 18, 2009) (2 pages) http://www.medicaldevicestoday.com.

Cribier et al., "Transcatheter Aortic Valve Replacement: The Future is Here!", Service de Cardiologia, Hopital Charles Nicolle pp. 1123-1125 (2008), Rouen, France.

Glower et al., "Minimally Invasive Direct Aortic Cannulation With Endo-Aortio Occluson", The EndoDirect System (pp. 1-16).

Capio™ Suture Capturing Device, "Reach: Throw and Capture: One Step. One Device", Boston Scientific Microvasive® (4 pages).

Covidien Endo Stitch™, "Suturing Made Easy" (4 pages)—www.covidien.com/autosuture.

Leigh, "Fig. 1. Fresh Porcine Heart Bursting Pressure Study Comparing Transapical Access Wound Automated Closures to Hand Sutured Controls", LSI Solutions (Jun. 21, 2010).

Knight et al. "Automated Remote Transapical Wound Closure System: Fresh Porcine Heart Bursting Pressure Study and Cadaver Endoscopic Demonstration", http://sts2011.abstractcentral.com (Jun. 16, 2010) (3 pages).

LSI Solutions®, RD Technology Guide (6 pages)—www.lsisolutions.com.

SEW-RIGHT SR•5™, The Single Squeeze suturing Device™, Copyright © 2003 LSI Solutions® (6 pages) www.lsisolutions.com.

SEW-RIGHT SR•5™ Device and SR•5™ Quick Load™, Designed by Sauer et al., document No. 020237-A, LSI Solutions™ (19 pages)—www.lsisolutions.com.

RD Running Device™, Surgery's Best Suturing Technology™, 2005 LSI Solutions® (2 pages) www.lsisolutions.com.

Medical Design Excellence Awards 2002, LSI Solutions (1 page).

International Preliminary Report on Patentability, dated Jan. 15, 2013 (6 pages) in corresponding International Patent Application No. PCT/US2011/039710.

* cited by examiner

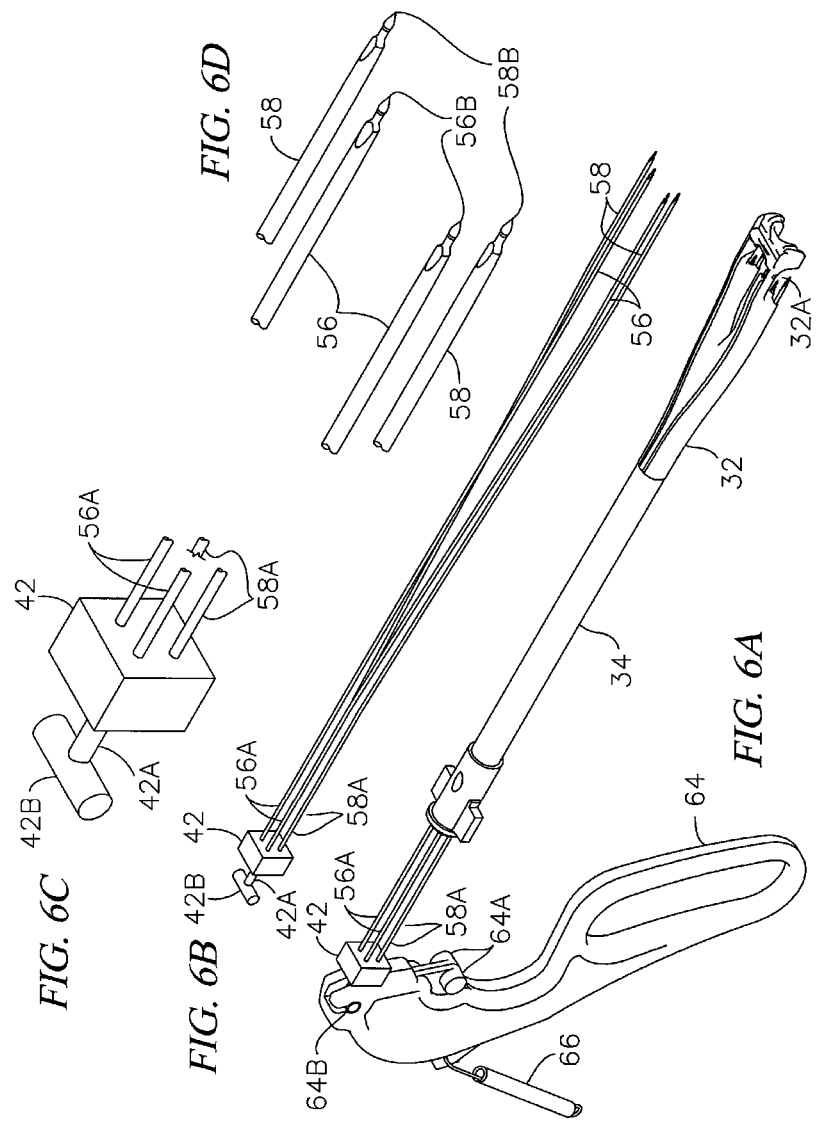

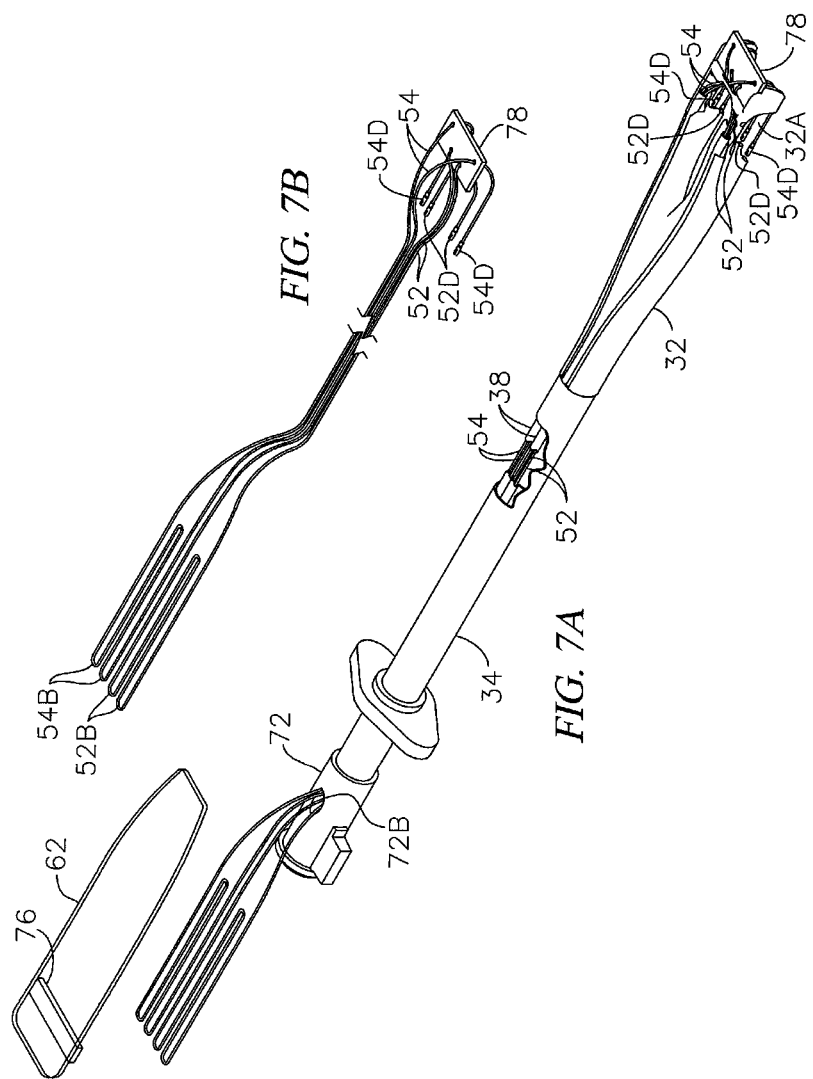

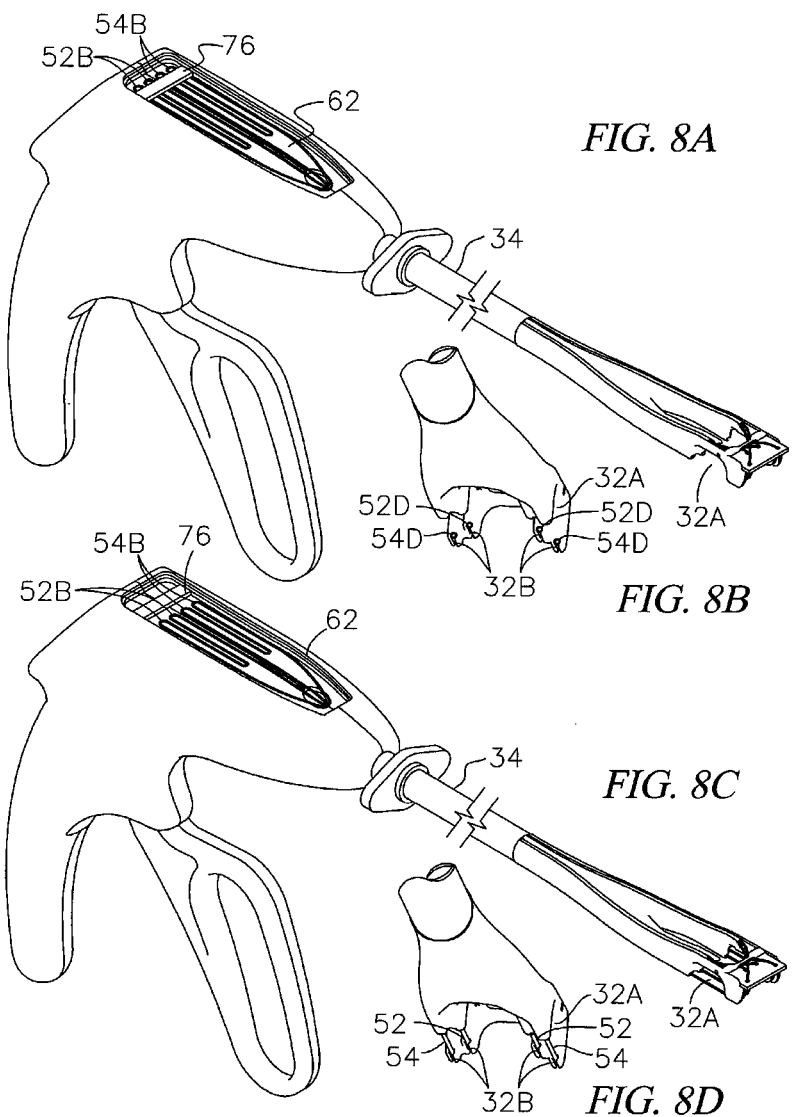

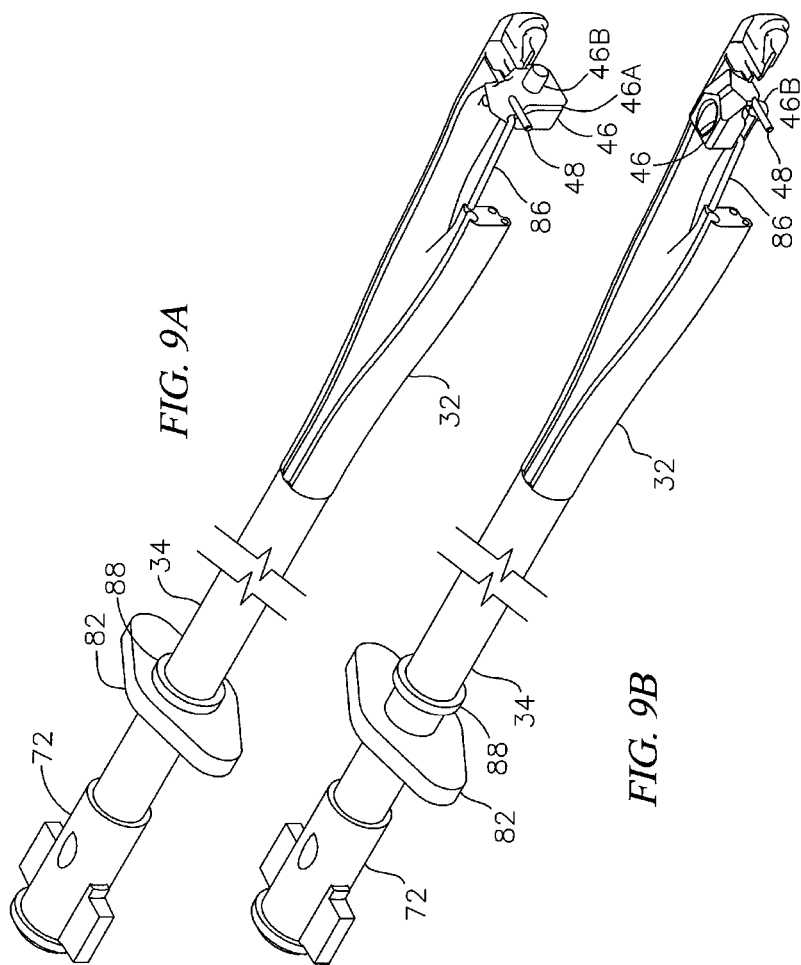

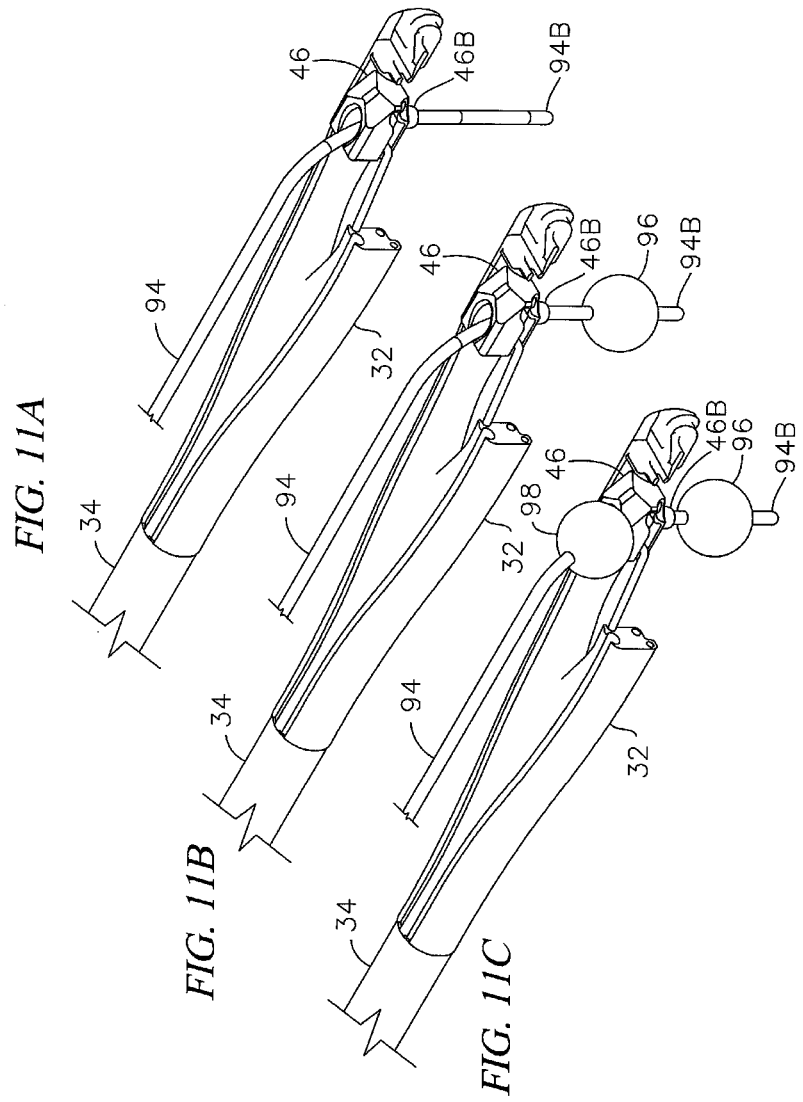

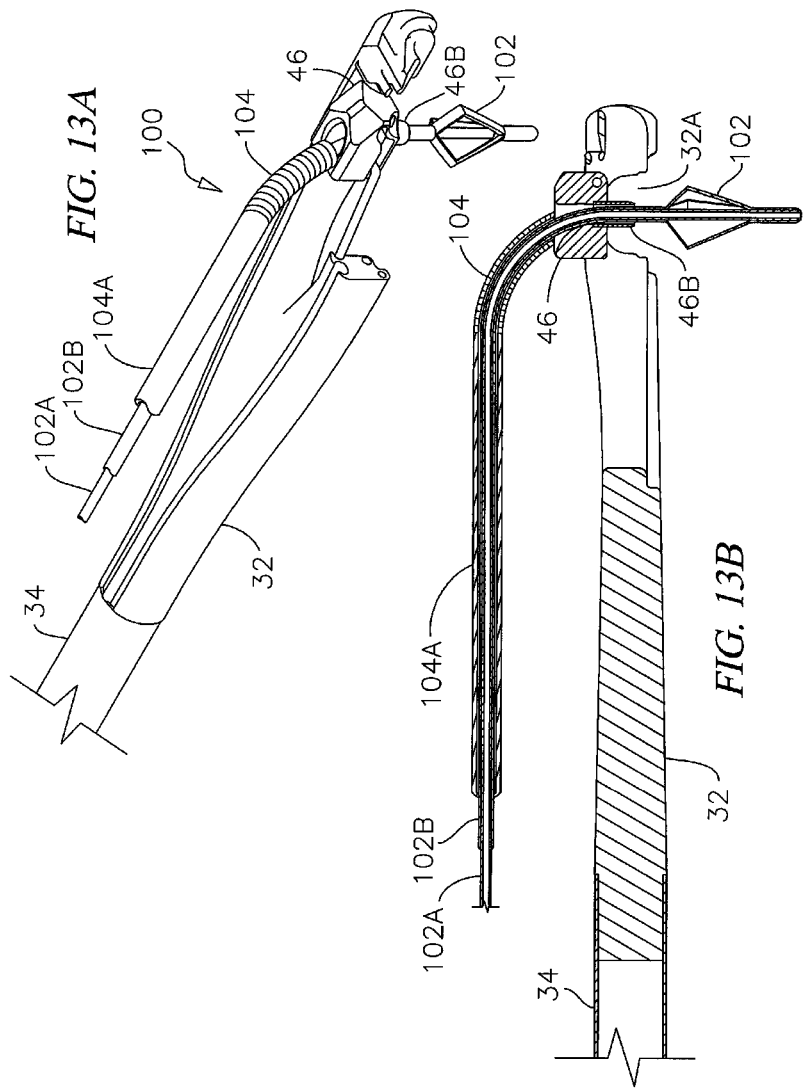

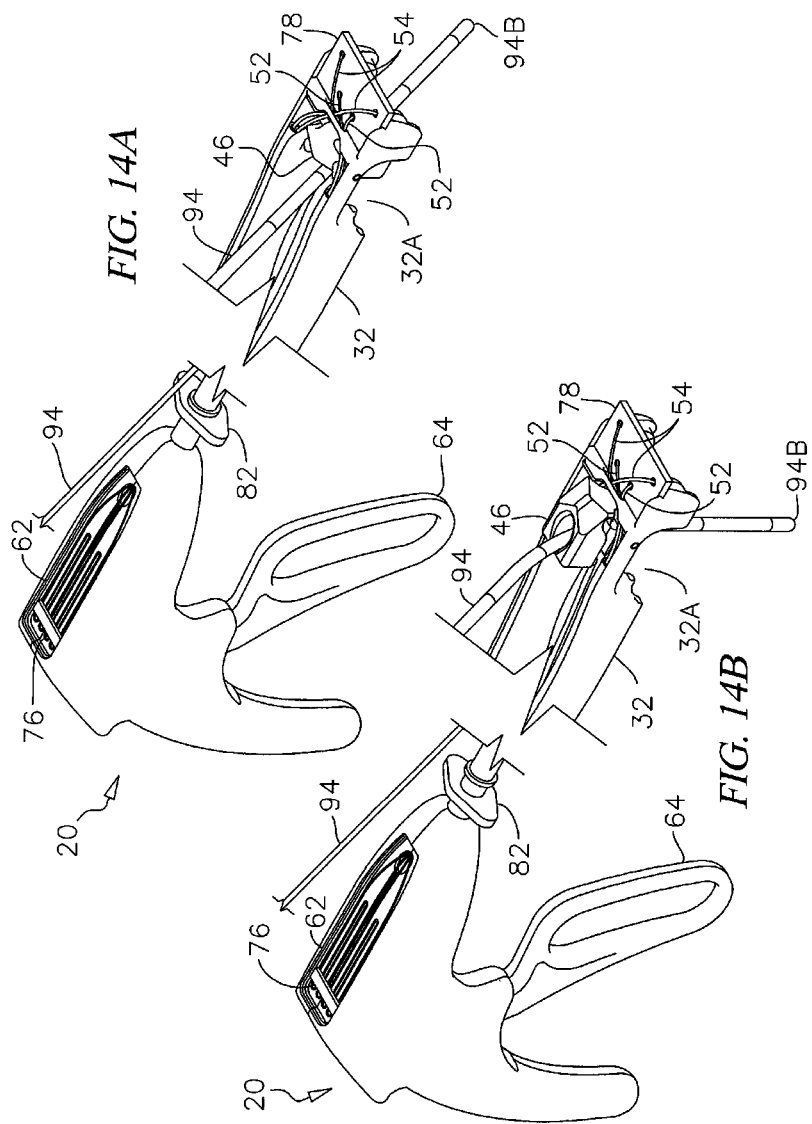

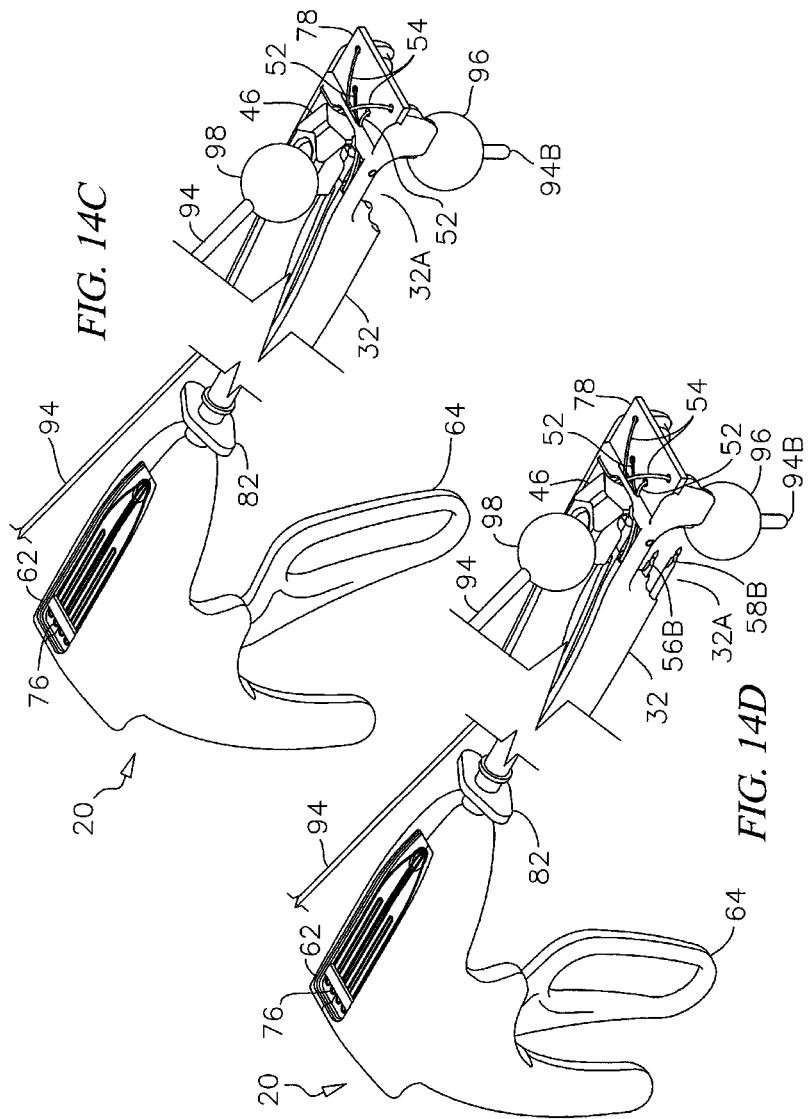

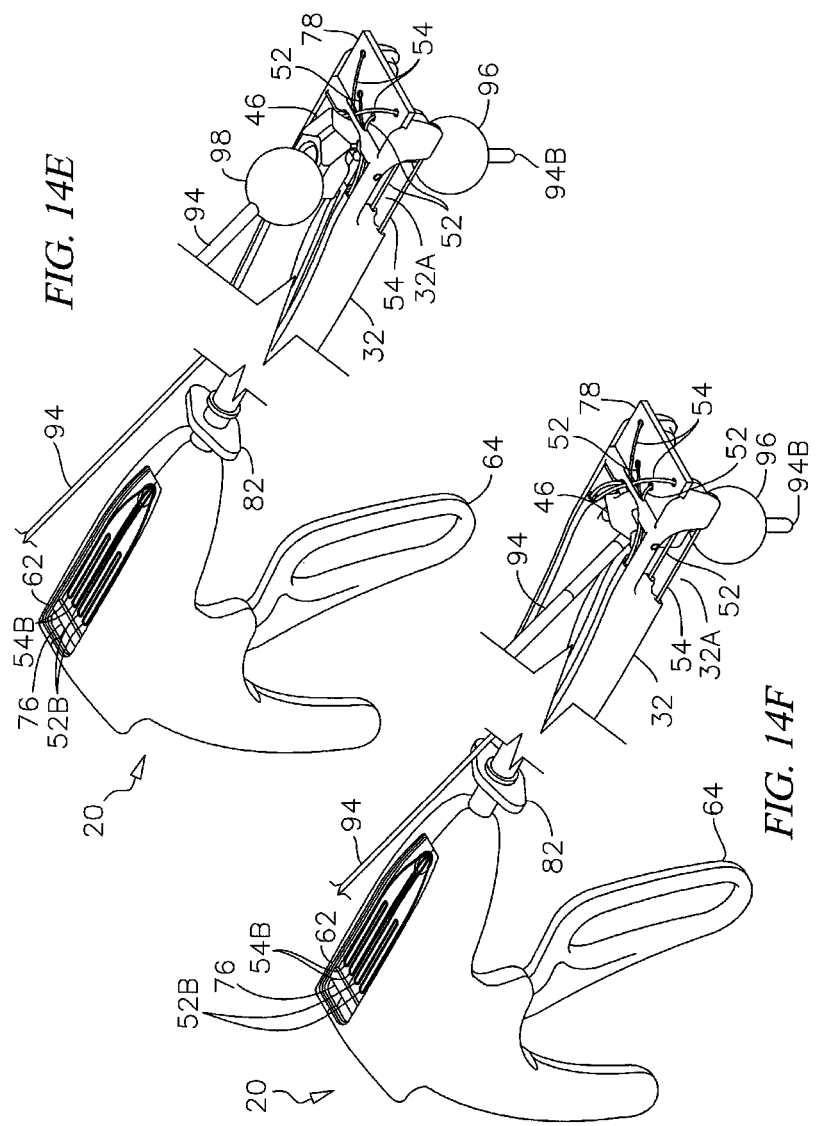

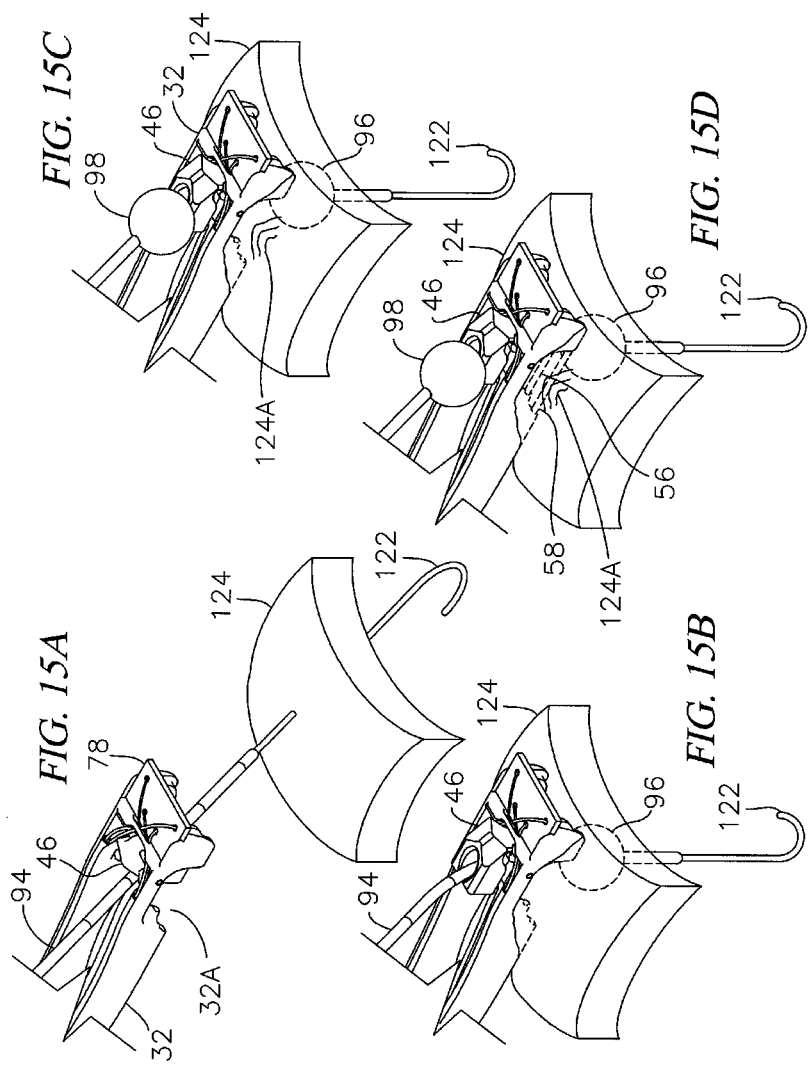

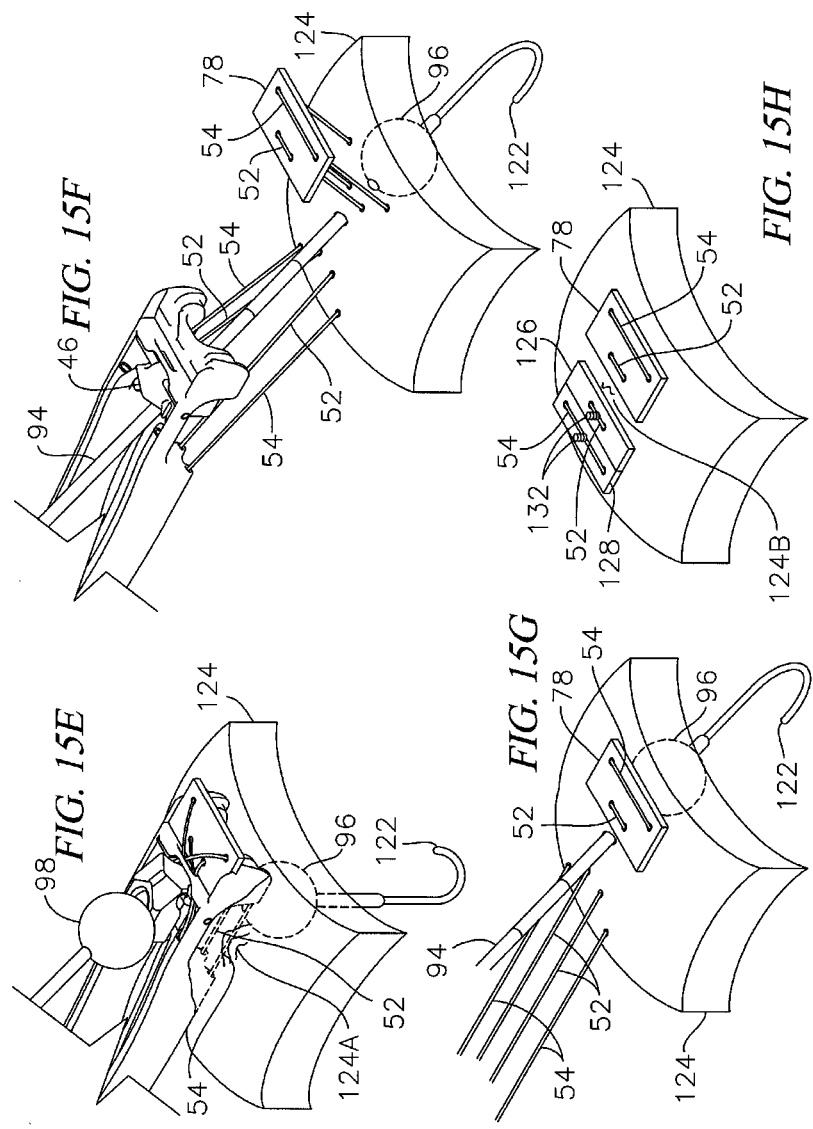

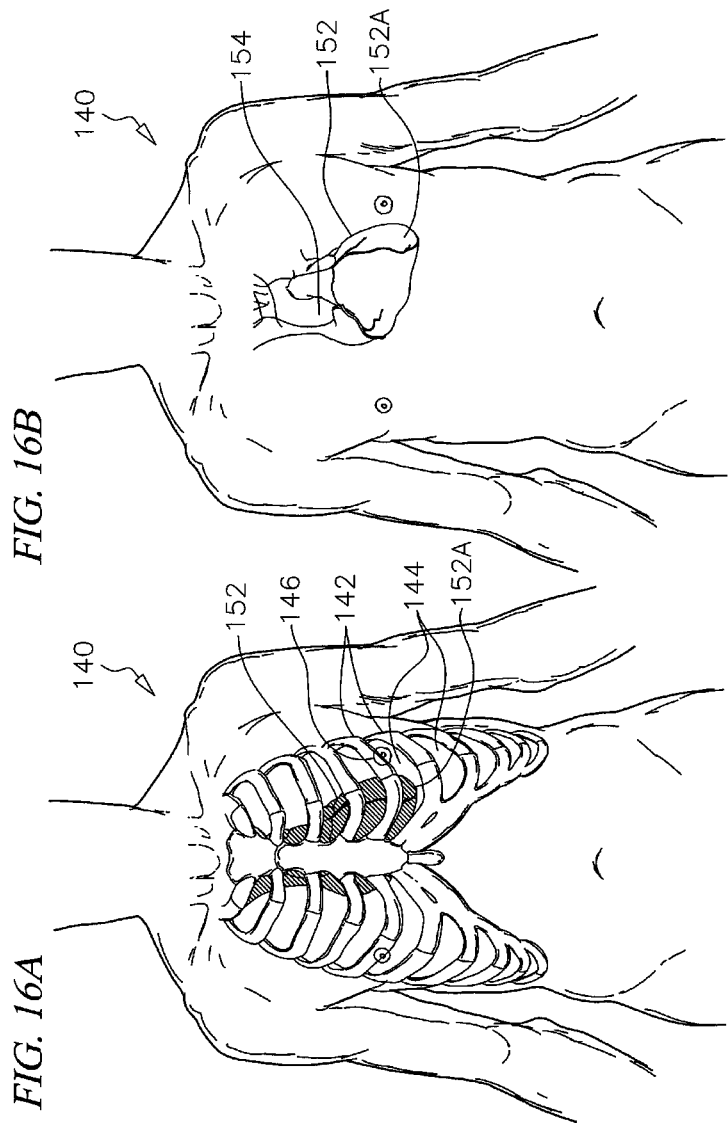

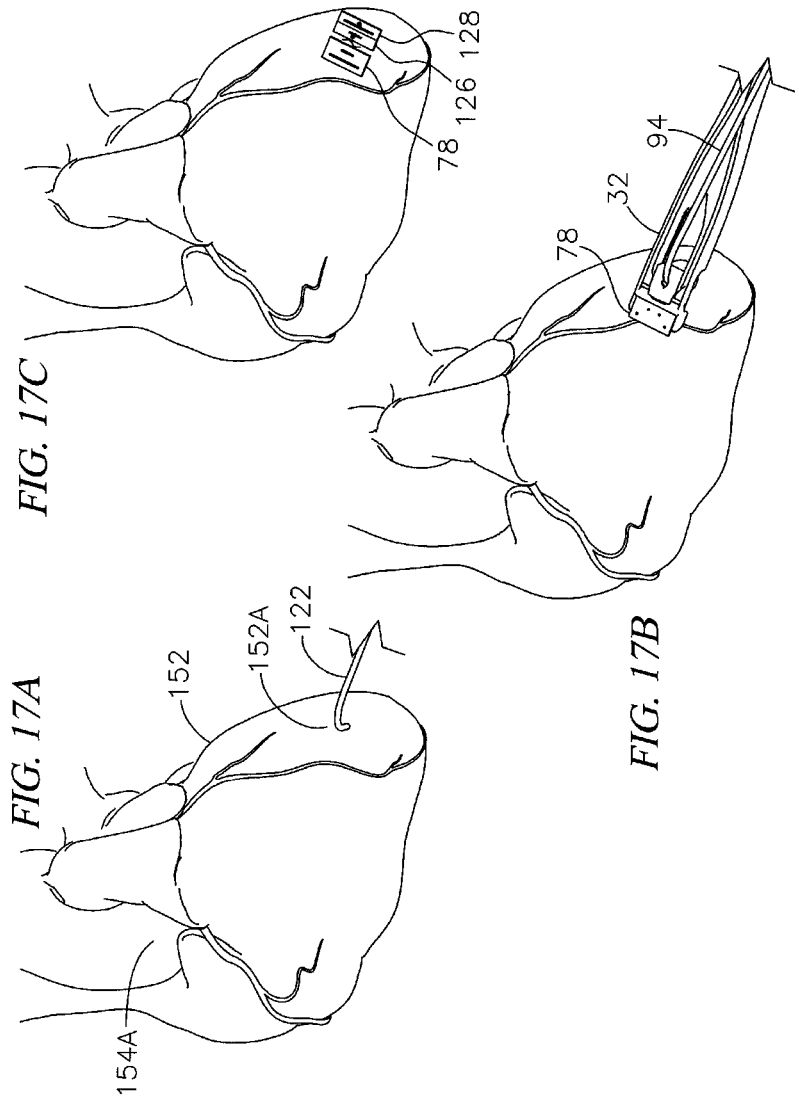

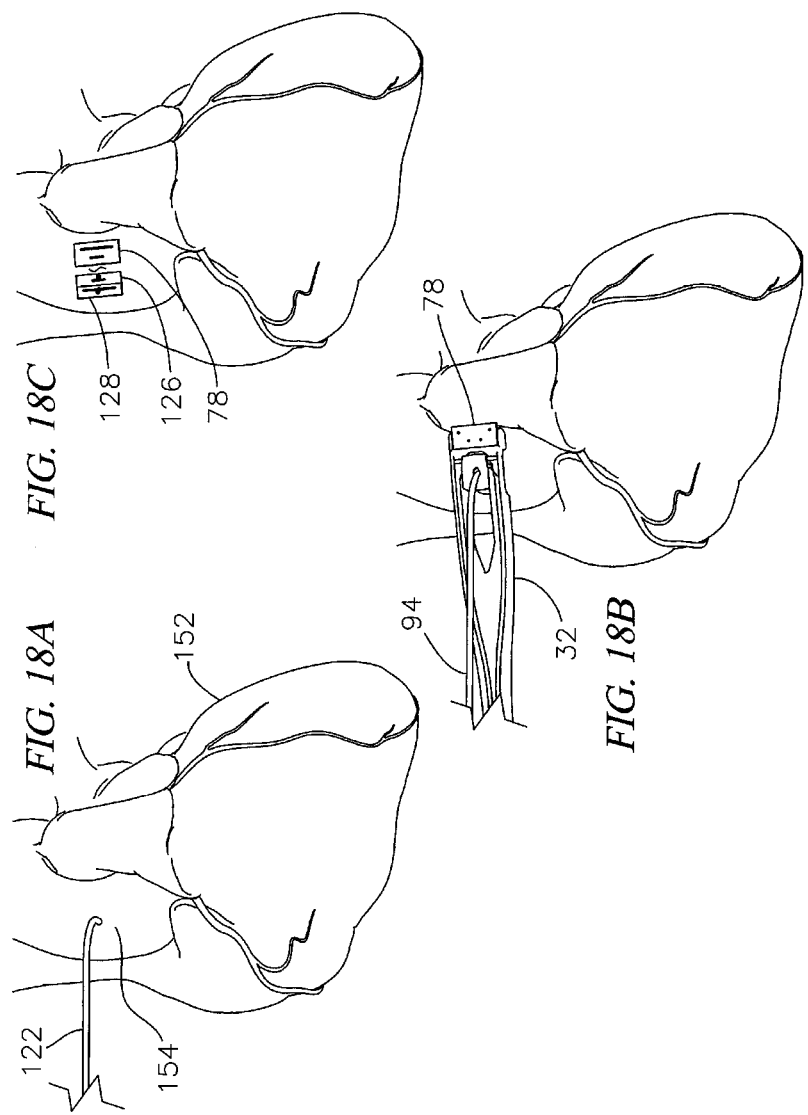

METHOD AND APPARATUS FOR CLOSING AN OPENING IN THICK, MOVING TISSUE

BACKGROUND OF THE INVENTION

1. Field of the Invention

This invention relates generally to new methods and devices for placing stitches in relatively thick, moving tissue so that when the ends of the suture are drawn tightly together, the tissue within the suture is constricted and more particularly to methods and devices for the minimally invasive remote simultaneous and hemostatic placement of multiple horizontal mattress sutures centered circumferentially around a placed guide wire traversing through a tissue wound site that will subsequently be enlarged (to provide a passageway to facilitate a medical intervention) and then hermetically closed. An embodiment of the invention includes a hand actuated suturing instrument with multiple needles that drive through relatively thick engaged tissue each picking up an end of a strand of suture for the precisely oriented suture placement at predetermined depths of multiple concentric horizontal mattress sutures with pre-loaded pledgets. To enable accurate device placement on a potentially moving tissue structures, such as a beating heart, this suturing instrument incorporates a novel low profile pivoting or rotating mechanical alignment guide to enable controlled positioning of the distal end of the instrument at the desired location identified by a temporary guide wire traversing and centered on the pending access site. In accordance with another embodiment, to maintain reliable purchase (i.e., engagement) on such thick, moving tissue structures, this invention provides an additional mechanical means to accurately and securely engage the suturing instrument's suture placement distal end with the targeted tissue site. Examples illustrating novel methods of the use of this invention for the safe and secure closure of transapical heart access wounds and ascending aorta cannulation sites are also herein described.

2. Description of Related Art

Wounds in living tissues and organs are often created by physicians to provide a passageway or access to more internal structures for diagnostic and therapeutic interventions. Access wounds made in tissue structures that are thicker walled, not fixed in position (e.g., mobile or actively moving) or acting as barriers to hold pressurized fluids or gases can be more challenging to establish and close. Temporary guide wires are routinely positioned at proposed entry wound sites to provide a central target and guiding element for improved device placement accuracy during tissue access. For example, for access to the inside of the beating human heart, transmyocardial cannulation of the lateral left ventricle near the apex permits accessibility through the ventricular chamber to the region of the aortic root, the mitral valve and the left atrium. Another cardiac intervention example is the cannulation of the anterior ascending aorta to provide a site for antegrade passage of oxygenated blood during cardiopulmonary bypass. Guide wires can be installed to better enable transapical access to the moving, contracting left ventricle along with transmural access to the pulsatile ascending aorta. While a number of techniques and technologies already exist for closing various types of wounds, the need still exists for improved means for closing many tissue wounds created for advanced minimally invasive interventions. This need is critical for closing wounds accessed remotely through small openings, and especially, for securing wound closures of relatively thick tissues containing pressurized fluids, such as circulating arterial blood.

While this invention can be used for securing a wide variety of tissue structures, it is particularly useful for thicker, non-fixed tissue, as is often encountered in cardiac interventions. Since the invention has multiple potential cardiac applications, abridged heart anatomy highlights are presented next. The healthy human heart has four chambers: the right atrium, right ventricle, left atrium and left ventricle. This critical circulatory system organ is generally considered to have a "right" side, in which the right atrium receives from the body deoxygenated blood that the right ventricle pumps to the lungs and a "left" side, in which the left atrium receives from the lungs oxygenated blood that the left ventricle pumps into the systemic circulation. To maintain normal unidirectional blood flow and physiologic pressures, hearts have four valves: the right atrio-ventricular tricuspid valve, the pulmonary valve between the right ventricle and the pulmonary artery, the left atrio-ventricular mitral valve and the aortic valve between the left ventricle from the ascending aorta.

Over the past decade, a growing appreciation has developed for the potential to surgically intervene on the inside of the beating heart through small access wounds made directly through the muscular myocardial wall, typically near the pointed tip or apex of the anterior left ventricle. This so-called, Transapical Access approach has been proposed for interventions ranging from atrial endocardial ablations to mitral valve repairs to transcatheter aortic valve replacements. Transapical aortic heart valve replacement procedures are now in clinical use in Europe and North America.

A brief review of transapical endocardial ablations and mitral valve repairs include, for example, Lattouf (Pub. No: US2007/0270793 A1) proposed accessing the interior chamber of the left atrium via a penetrating access wound in the left ventricular apex wall, then retrograde through the chamber of the left ventricle and the mitral valve. After accessing the chamber of the left atrium and destroying the aberrant endocardial tissue, the apical closure was left to be performed by open traditional surgical techniques requiring a painful highly invasive thoracotomy incision in the chest wall. Lattouf also teaches (U.S. Pat. No. 6,978,176 B2) a method and devices for repair of the mitral valve's chordal attachments anchored within the left ventricle; they propose using a plastic plug for cannulation of the apical access wound, anchoring the new mitral chordal repair filaments and closing the apical wound. Gammie (U.S. Pat. No. 7,635,386 B1) showed a similar transapical approach to mitral valve repair with a different suturing device.

Transcatheter transapical aortic valve replacement is an area of concentrated research and significant clinical excitement at this time. At the May, 2010 American Association of Thoracic Surgeons, over twenty different presentations were offered on this subject; none offered minimally invasive or single port access or percutaneous technology for a least invasive route for transapical interventions. Reviews of the published literature on this subject demonstrate that no means currently exists clinically or proposed in research that has been publically offered for the minimally invasive closure of a transapical access site. Transcatheter transapical aortic valve replacement is currently reserved for the sickest cardiac patients, who are usually quite elderly, with multiple other co-morbidities and dying from otherwise inoperable critical aortic stenosis disease. A true minimally invasive access option would offer these highly compromised patients their best chance for a safe recovery.

While transcatheter transapical heart valve replacement products are already helping many patients, especially in Europe, until now an excellent means to remotely close transapical access wounds has remained elusive. Edwards® Lifesciences® provides the 31 Fr. Ascendra® transapical delivery system for 23 and 26 mm stainless steel bovine pericardium balloon expandable aortic valve xenografts; their full product launch is expected around 2012. In Europe, Medtronic® sells its Core Valve® re-valving system which incorporates a porcine aortic valve on an hourglass shaped nitinol frame, which is self expanding at body temperature. Medtronic's® Embracer® transapical delivery system products along with its Ventor® transfemoral versions are expected to be both released in 2014. The Medtronic® delivery system is 18Fr. and delivers valves that ultimately expand out to 20 and 27 mm. Medtronic® Melody® transcatheter pulmonary valve was first available in the United States in 2010. Other international companies, such as St. Jude Medical®, are reporting the development of transcatheter transapical valve products. To our knowledge, despite the clear need acknowledged for over the past half-decade, no one has yet reported an automated technology to facilitate truly minimally invasive transapical access site wound closure.

Many critically ill cardiac patients need their heart valves replaced, but no one would prefer a significantly large chest wall wound if a less traumatic, safe and effective alternative were clinically available. The first patient transcatheter aortic valve replacement occurred in France in 2002. Now, an estimated 50 transapical aortic valve replacement procedures occur each week throughout the world; all of these critically ill patients have required open chest surgery predominantly through the anterior lateral $6^{th}$ costal interspace. This open technique is to expose the front of (i.e., the anterior surface of) the beating heart to enable traditional hand suturing techniques for preparation of the heart transapical access site. Hybrid operating rooms offer the convergence of interventional cardiology techniques with the effectiveness of heart valve replacement, which until recently required the direct application of the skilled hands of a cardiac surgeon. This modern collaboration will remain limited until a safe and reliable technology and techniques for truly minimally cardiac transapical interventions are available.

Over the past 5 decades, millions of patients have benefitted from cardio-pulmonary bypass to enable extracorporeal oxygenation and pressurization of blood reintroduced back into the open-heart surgery patients circulation during arresting of the heart. A common technique to provide a conduit for returning oxygenated blood back into cardio-pulmonary bypass patient's systemic circulation involves cannulating the patient's ascending aorta with a tube carrying pressurized oxygenated blood to provide access to the systemic circulation above the cross clamped aortic root. A better, less invasive means is needed for installing perfusion cannula tubes and subsequently closing an aortic cannulation site wound.

Many minimally invasive cardiac surgical procedures still require an arrested heart to ensure an effective intervention and enable required visualization. The patient can benefit enormously from the much smaller chest wound utilized for a minimally invasive mitral valve repair and still receive a long-term therapeutic effectiveness. Hand sewing a traditional double purse string suture into the ascending aorta through a minimally invasive small remote port site using standard needle drivers is so challenging that for most surgeons it would not be worth the additional risks. To avoid the direct transmural cannulation of the ascending aorta minimally invasive heart surgery, several suboptimal products are available. For example, Edwards® Lifesciences® offers a long balloon catheter, called EndoDirect®. This product can be threaded retrograde through the pulsating femoral artery in the groin up beyond the arch of the aorta, where its balloon is infused to occlude the most proximal aorta and permit infusion of pressurized, oxygenated blood into systemic circulation during iatrogenic cardiac arrest. These balloons tend to migrate to less appropriate locations and frequently require repositioning. Any catheter traversing the arch of the aorta risks displacing embolic material and inducing stroke and other complications. The large transmural wound in the femoral artery typically requires open surgery for arteriotomy repair. A minimally invasively delivered device to secure an aortic cannula during cardio-pulmonary bypass and to subsequently hermetically close the transmural access wound site would be a significant advance.

With the Minimally Invasive Surgery (MIS) revolution, several available suture placement products have offered surgeons working through small access sites alternatives to hand suturing and hand knot tying. The use of non-specialized laparoscopic or thoracoscopic needle drivers presents significant limitations to ergonomic and accurate remote suture placement. MIS suturing devices, such as the LSI SOLUTIONS® Sew-Right® SR●5® (U.S. Pat. No. 5,431,666) and Running Device® (U.S. Pat. No. 7,407,505 B2) along with their TK-5® Ti-Knot® technology, Covidien's® Endostitch and Boston Scientific's® Capio®, provide shafted instruments for placing suture remotely. None of these products readily permits the accurate and simultaneous placement of concentric sutures at the tissue locations required in the applications.

Another related category of remote suturing instruments are usually called trocar wound closure devices, which are typically used to close the access site wound at trocar cannulation sites in the anterior abdominal wall. Typically these devices are suture mediated and their device distal ends enter the hole they are intended to close, which may be problematic in the above mentioned examples. These types of devices also typically close holes that are not associated with pressurized fluids, like blood. While many variations of trocar wound closure devices have come into use over the past two decades (U.S. Pat. Nos. 5,368,611 and 5,620,456), none are known to enable this transapical wound or aortic cannulation site preparation and closure.

Arteriotomy wound closure devices are another group of products that can be used to close some vascular wounds (e.g., a femoral artery percutaneous access site in the groin). Several suture mediated devices have been described to offer puncture wound closure options; U.S. Pat. Nos. 5,766,183; 6,368,334 B1; 6,641,592 B1 cover such technology. Alternatively, metal clips opposing wound edges U.S. Pat. No. 4,929, 240 and absorbable plugs U.S. Pat. Nos. 4,852,568 and 5,342, 393 were developed. Since these devices have also been available for some time, they appear unacceptable for the proposed related applications, including transapical access and aortic cannulation site closure.

A previous invention (Medical Instrument To Place A Pursestring Suture, Open A Hole And Pass A Guidewire, U.S. Pat. No. 7,731,727 B2) is somewhat similar in appearance to the current invention but has many distinct differences. The previous technology is remotely applied to thin walled tissue, which is sucked into place by vacuum for needle deployment using an integrated vacuum chamber; this tissue, such as stomach or rectal wall, needs to be highly conformal to avail itself to vacuum mediated deformation. Thicker walled structures may not be held reliably enough by vacuum alone. This previous instrument is not intended for use on tissue which is acting as a barrier to hold back pressurized fluids. The needles generally penetrate the full thickness of the tissue, which could cause immediate leakage of the pressurized fluid. Also the use of integrated cutting blade could cause an immediate hemorrhage, for example, in a beating heart. In addition, with this vacuum mediated technology, the guide wire is through the instrument at the end of the procedure after the purse string suture is placed and the transmural incision has been made; this is opposite of the current invention which traverses a pre-placed guide wire. In accordance with the present new invention for use with thicker tissue, the device end is inserted onto and follows an already existing temporary guide wire, which was previously installed to serve as a guide to the targeted tissue site. The previous technology does not teach a mechanical instrument-to-tissue alignment mechanism or an instrument-to-tissue secure engagement means based on compression between external and internal anchors. The previous technology was not intended for use with thick walled moving structures.

Despite a long recognized critical clinical need, no technology is known to exist that provides for the safe and effective minimally invasive closure of certain access wounds required for many therapeutic interventions, especially several related to cardiac procedures involving thicker tissue. This innovation now offers a new potentially highly effective and safe option for future patients.

BRIEF SUMMARY OF THE INVENTION

The surgical act of placing one or more filamentous structures through a single or multiple tissue sites is often called suturing or stitching. The filamentous structure itself, such as a string, cord or wire which can be made of a wide variety of materials including cotton, silk, plastic polymer, metal, etc., is referred to as a suture or stitch. The process and location of placing a single segment of suture through tissue is called "taking a bite" of tissue and "the bite", respectively.

A horizontal mattress suture, alternatively also described as a U-stitch after its shape, involves employing a single suture for placing (i.e., running) two parallel tissue bites located usually at approximately the same depth in the tissue and separated from each other by an area of tissue. Usually the length of each tissue bite is approximately the same; therefore, the distance in tissue from where one end of the suture enters and exits the tissue is comparable to the distance spanned in adjacent tissue by the other end of the suture. The simplest horizontal mattress suture constructed can be described as an inverted three-sided flat bottomed U-shape or, more simply, an open box. The flat bottom of the open box is outside of the tissue, two segments of contiguous sutures are placed into the tissue perpendicular to the bottom of the open box, parallel to each other and passing out of the tissue in the same direction. By connecting (outside of the tissue) one exiting suture end to the other suture end, a four-sided, closed box, square or rectangular suture configuration is developed. By pulling the suture end tighter, the tissue held between the tissue bites is drawn or tightened together. Such a surgical technique is known for holding tissue or wounds in apposition for healing, for controlling bleeding or both.

The present invention reliably places two concentric horizontal mattress sutures around a targeted tissue site, which can be thicker walled and potentially moving. To protect a suture closure site, an additional element called a pledget is sometimes used. The pledget, also called a bolster, can be made from sturdy but soft and compliant pad-like material, such as Teflon cloth or rolled cotton linen. The pledget is placed between the narrow suture and the delicate tissue to avoid overly compressing the tissue with the suture during tightening and healing. The outside segment of both sutures at the flat bottom of the box passes over a central portion of a single four holed pledget held in the distal end of the device. The two ends of each suture pass through four corresponding holes in the pledget so that after taking the four tissue bites, the pledget is pulled down onto the tissue. To close the top of the box, a second single four holed pledget or alternatively two, two holed pledgets can be used to secure the free ends of the suture that have exited the proximal side of the tissue suturing site. The free ends of the suture pass through holes in the pledgets and provide a cushion buffer between the knotted suture connection and the underlying tissue. Knotting or otherwise securing the suture together essentially permanently closes the top of box and compresses together the tissue between the sutures and pledgets.

This is a novel suturing instrument for the remote placement of multiple pledgeted sutures centered circumferentially surrounding a targeted tissue wound site in relatively thick and less compliant tissue, such as the beating heart and aortic wall structures. Its sutures are precisely delivered to predetermined tissue depths and for pre-set distances. It does not require the distal end of the device to enter the wound site and can place the secure sutures around an existing guide wire before the access wound is fully opened. The suturing instrument includes a pistol grip style handle and a hand actuated lever for the precise placement of multiple pledgeted horizontal mattress sutures at the targeted access site, such as the anterior surface of the heart near its apex or the ascending aorta. The shaft of the instrument connects at its proximal end to the handle, which remains outside of the patient and in direct control of the surgeon. For example, in creating and closing a transapical access site, the shaft enters and traverses the patient's body at the left chest wall to deliver the device distal end where suture placement occurs to the targeted anatomic location (e.g., the apex of the beating heart).

This suturing instrument incorporates a low profile rotating, lockable, mechanical tissue alignment guide to enable more automatic controlled positioning of its distal end at its desired tissue location. The unlocked alignment mechanism rotates to allow the device end and its indwelling guide wire to pass more freely through narrow openings. When locked, the alignment guide provides a stable guide mechanism orienting the indwelling guide wire in a favorable position perpendicular to the tissue receiving jaw or welting trough of the suturing instrument for placing the sutures.

Further, this instrument provides a mechanical assembly to accurately and securely engage the distal end of this suture delivery instrument with the targeted tissue site. One tissue engagement assembly provides two linked balloons. When both balloons are filled and expanded, a tissue ridge or welt is compressed and sandwiched in the space between the balloons and the receiving gap or welting trough in the distal end of the instrument, thereby moving and re-conforming the targeted tissue into the most appropriate suturing position. An alternative tissue engagement assembly provides an expandable, mechanical assembly such as an internal hinged mechanical anchor that pulls tissue up into the suturing position against the welting trough in the undersurface of the suturing jaw, while an external compression spring exerts force on the top of the rotating alignment guide mechanism to further press the welting trough onto the tissue suturing site.

The results of current research involving this invention were recently submitted for presentation at the 2011 Society for Thoracic Surgery's Annual Conference. This submission is entitled, "Automated Remote Transapical Wound Closure System: Fresh Porcine Heart Bursting Pressure Study and Cadaver Endoscopic Demonstration." Abridged highlights from this research submission include:

Transcatheter therapies are rapidly becoming mainstream for the treatment of structural heart disease. A transthoracic non-rib spreading single port option providing short distance, non-torturous direct access and including a secure transapical wound closure could further advance the benefits of this antegrade procedure.

Anterior left ventricular transapical access wounds in 50 porcine (47 ex vivo, 3 beating) and 10 human cadaver (8 open, 2 endoscopic) hearts were all successfully closed during the development of this hand activated remote suturing technology, which places two concentric pledgeted horizontal mattress sutures at precise depths ranging from 3 to 5 mm. Routine wound closure time was less than 2 minutes. For this bursting pressure study, a clinically available dilator was used to create transapical wounds through freshly harvested porcine hearts, in which automated (N=10) and hand sutured closures (N=5) were tested for leakage by pressurized saline infusion. This technology was used through a thoracotomy to close transapical wounds in the beating hearts of three non-survivor pigs. Human cadavers received automated transapical wound closures via this videoscopic single port technique.

All dilated then closed transapical access wounds sutured throughout this development project were hermetically closed. In the fresh porcine heart bursting pressure study, the first two hand sutured control closures received fully transmural sutures; both showed sustained leakage isolated to the suture tracks at 222 and 298 mm Hg mean peak. All other closures remained leak free despite high intraventricular infusion pressures (mean, min., max in mm Hg, automated: 327, 262, 348 and hand sutured: 303, 222, 358) causing this ex vivo model's heart valves and atria to fail so that greater pressures could not be generated. Videos illustrate the extent of distention of the infused hearts tested in this study. The porcine beating heart closures were hemostatic. Endoscopic videos show the ease of use of this method for single port closure of transapical access sites in the human cadaver model.

Advanced customized tools are needed to assure cardiothoracic surgeons continue to lead in the critically important arena of minimally invasive therapeutic heart procedures. This automated transapical access wound closure technology and technique developed for endoscopic use was demonstrated to be ergonomic, fast, effective and highly reliable. The fresh porcine heart bursting pressure study showed these remote suture mediated wound closures remained hermetic beyond the supra physiologic infusion pressures intolerable to other structural elements of the hearts tested in this model. The early successful results illustrating hemostatic closures in porcine in vivo beating hearts and transthoracic totally endoscopic apical closures through a single port in the human cadaver model encourage further evaluation.

BRIEF DESCRIPTION OF THE DRAWINGS

The foregoing objects, features and advantages of the invention will become more apparent from a reading of the following description in connection with the accompanying drawing, in which:

FIG. 6A is a perspective view highlighting the needle drive components of FIG. 3;

FIG. 6B is a perspective view of the needle connecting fixture and the four needles;

FIGS. 6C and 6D are blown-up perspective views of the proximal and distal ends, respectively, of the needles of FIG. 6B;

FIG. 7A is a perspective view showing the suture and pledget storage features of FIG. 3;

FIG. 7B shows the ferrules at each end of both strands of suture and both sutures incorporated through a single pledget and the indicator suture loops of FIG. 7A;

FIG. 8A is a partial perspective view of the instrument of FIG. 1 highlighting the tell-tale suture loops proximal to the suture pad seen through the handle window indicating the ferrules are in their ferrule compartments;

FIG. 8B is a partial perspective view of the distal end of the instrument of FIG. 8A shown from underneath to highlight the ferrules in place in the distal side of the jaw;

FIG. 8C is a partial perspective view of the instrument similar to FIG. 8A except now the suture loops are distal to the suture pad as seen through the handle window indicating the ferrules are retracted back and showing the sutures spanning the welting trough of the instrument;

FIG. 8D is a partial perspective view of the distal end of the instrument of FIG. 8C shown from underneath to highlight the sutures now traversing the welting trough;

FIG. 9A is a partial perspective view of components of the pivoting mechanical alignment guide of the instrument of FIG. 1 showing the lock control knob fully forward and the mechanical alignment feature unlocked;

FIG. 9B is a partial perspective view of components of the mechanical alignment guide of the instrument of FIG. 9A showing the lock control knob in the fully back, locked position and the mechanical alignment guide rotated up and locked in place;

FIG. 11A shows a perspective view of tissue engagement assembly before activation of either balloon;

FIG. 11B shows a perspective view of the tissue engagement assembly with its internal engagement balloon expanded;

FIG. 11C shows a perspective view of the tissue engagement assembly with both its internal engagement balloon and its external engagement balloon expanded;

FIG. 13A shows a partial perspective view of a second embodiment alternative tissue engagement assembly that provides a mechanical expandable hinged frame internal tissue engagement anchor and a compressive spring mechanism for external engagement;

FIG. 13B shows a section view of FIG. 13A;

FIG. 14A shows a partial perspective view highlighting the instrument's distal end with the alignment mechanism unlocked, both tissue engagement features not expanded, the suture and pledget in the loaded configuration and the needles fully retracted;

FIG. 14B shows a partial perspective view highlighting the instrument's distal end with the alignment mechanism locked, both tissue engagement features not expanded, the suture and pledget in the loaded configuration and the needles fully retracted;

FIG. 14C shows a partial perspective view highlighting the instrument's distal end with the alignment mechanism locked, both tissue engagement features expanded, the suture and pledget in the loaded configuration and the needles fully retracted;

FIG. 14D shows a partial perspective view highlighting the instrument's distal end with the alignment mechanism locked, both tissue engagement features expanded, the suture and pledget in the loaded configuration and the needles partially advanced;

FIG. 14E shows a partial perspective view highlighting the instrument's distal end with the alignment mechanism locked, both tissue engagement features expanded, the pledget in the loaded configuration, the ferrules, attached sutures and the needles fully retracted;

FIG. 14F shows a partial perspective view highlighting the instrument's distal end with the alignment mechanism unlocked with the inner tissue engagement balloon still expanded, the outer tissue engagement balloon not expanded and with the needles, ferrules and sutures fully retracted back, while the pledget remains in the loaded configuration;

FIG. 15A is a partial perspective view of the instrument's distal end with the loaded alignment guide being fed over a guide wire and co-axial to the common balloon tube towards a tissue site;

FIG. 15B is a partial perspective view of the distal end of the instrument in place on the tissue site with the tissue alignment feature in the locked up position and the internal balloon expanded;

FIG. 15C is the same as FIG. 15B except now the external balloon is also expanded to compress the welting trough to the tissue held between the two expanded balloons;

FIG. 15D is a partial perspective view showing the welting trough in place compressed between the balloons; hidden lines are used to indicate the needles passing through the tissue;

FIG. 15E is similar to FIG. 15D except now the hidden lines indicate sutures that now traverse the tissue bite;

FIG. 15F shows the distal end of the instrument with the mechanical alignment feature in the unlocked position being pulled away over the common balloon tube and guide wire from the tissue site with the suture paying out and the pledget coming down onto the tissue;

FIG. 15G shows the tissue closure site after complete removal of the instrument distal end with the pledget in place, the proximal sutures exiting the tissue, and the internal balloon still expanded in place;

FIG. 15H shows the wound closure site with both pledgeted horizontal mattress sutures secured in place at the targeted tissue site;

FIG. 16A is an illustration of thorax of an elderly man with the rib structures highlighted overlying a silhouette of the heart;

FIG. 16B is the same elderly man's thorax now with the rib structures removed to highlight the location of the heart in the human chest;

FIG. 17A is the schematic representation of the human heart with a guide wire entering the apical "bald spot" on the left anterior surface of the left ventricle;

FIG. 17B shows the distal end of the instrument of the present invention in place over the guide wire secured against the apex of the left ventricle, prior to expanding the external balloon;

FIG. 17C shows the closed apical access site secured between the pledgeted horizontal mattress sutures;

FIG. 18A is a schematic of the human heart with a guide wire shown entering the anterior surface of the ascending aorta;

FIG. 18B shows the distal end of the instrument of the present invention positioned onto the anterior surface of the ascending aorta prior to expanding the external balloon;

FIG. 18C shows the pledgeted double mattress suture wound closure site on the anterior ascending aorta.

DETAILED DESCRIPTION OF THE INVENTION

In accordance with a presently preferred embodiment of the invention, a remote suturing instrument is provided for the precise placement of multiple pledgeted horizontal mattress sutures at a guide wire targeted location in a predetermined orientation, depth and length for securing thicker, less compliant tissue structures. An embodiment of the innovation disclosed here includes a multiple needle drive feature along with a pledgeted suture storage and release concept, a rotating tissue alignment guide mechanism, which includes an extended tube, and two alternative mechanical tissue engagement assemblies (one incorporating balloons and the other a hinged anchor and compression spring) to better hold and position the tissue for suturing.

Figure 1:
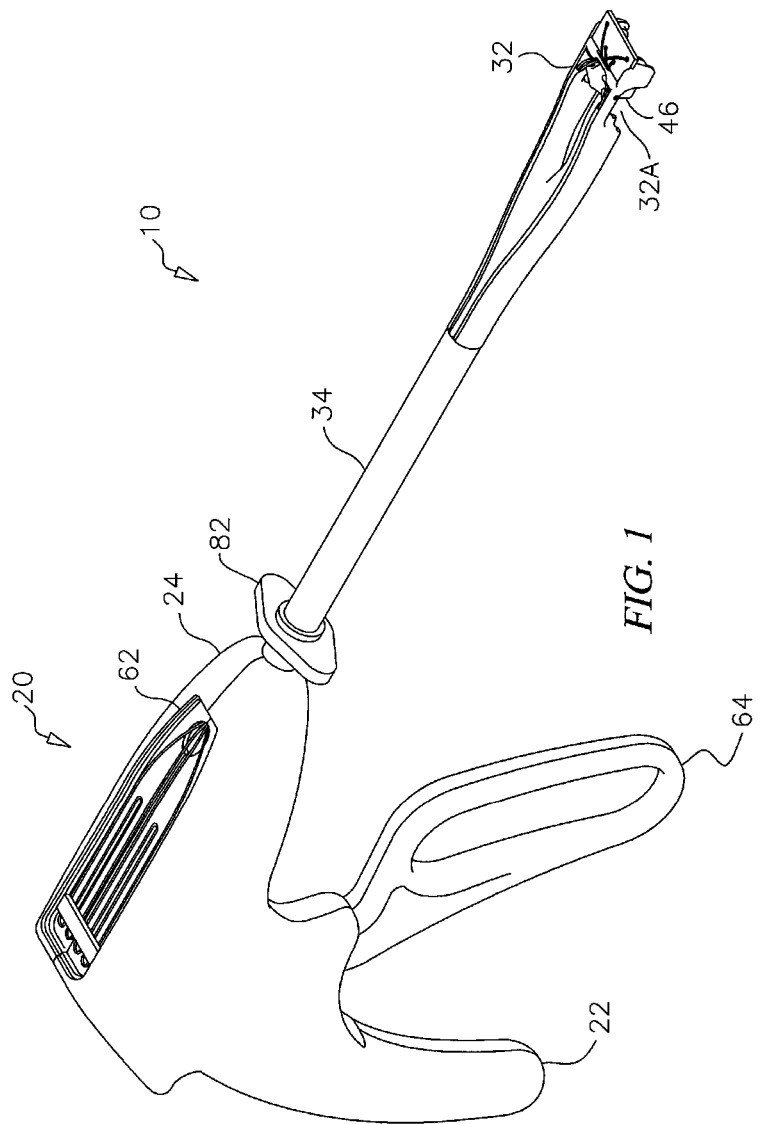
FIG. 1 is a perspective view of a preferred embodiment of a tissue suturing instrument of the present invention.
Figure 2:
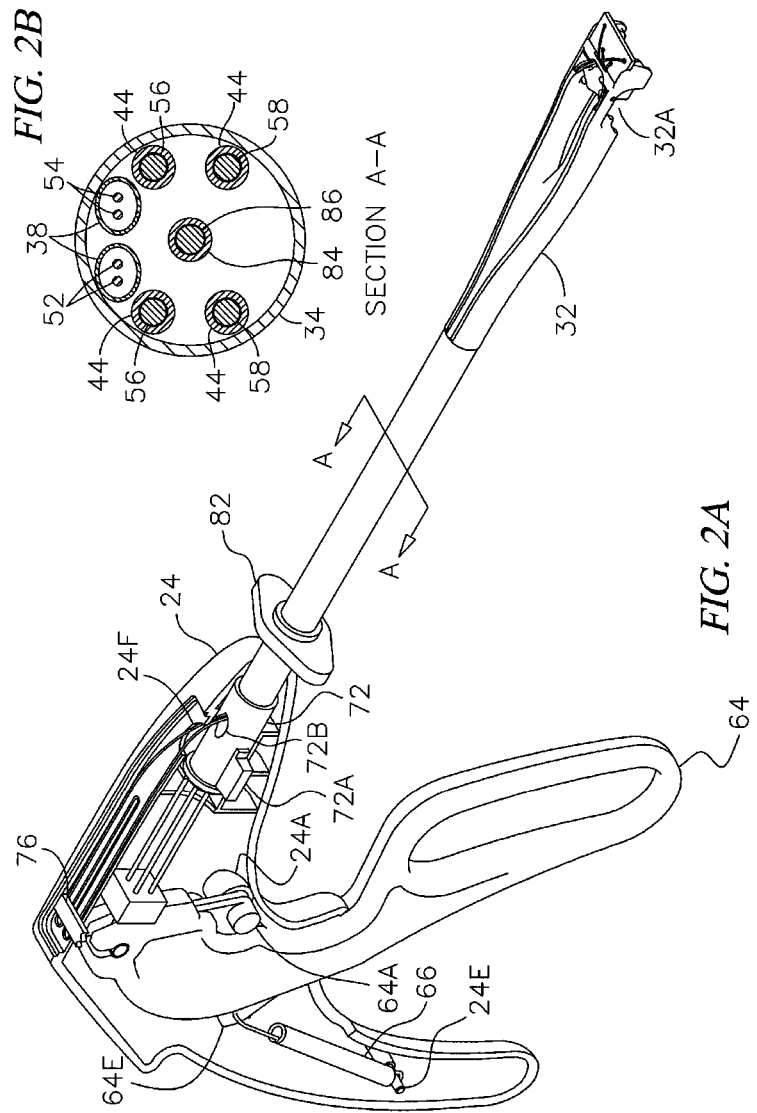
FIG. 2A is a perspective view of the tissue suturing instrument of FIG. 1 in which the right cover of the housing of the instrument is removed.
FIG. 2B is a blown up cross-sectional view of the shaft elements along Section A-A of FIG. 2A.

FIG. 1 is a perspective view of a tissue suturing instrument 10 in accordance with a first embodiment of the present invention. A pistol grip style handle assembly 20 is constructed from a right handle portion 22 and a left handle portion 24 which are preferably made of an injection molded plastic or the like and to which subsequent components are attached. An elongated shaft tube 34 extends proximal from the handle to the distal end 32 of the instrument at which a tissue receiving jaw or welting trough 32A is located. A sliding lock control knob 82 is disposed on the proximal end of shaft tube 34 and can be slid towards the handle to lock a rotating mechanical tissue alignment guide 46 in its upward orientation. A suture viewing window 62 is preferably located on the top of handle 20 as is described in more detail below.

Now referring to FIGS. 1-4, certain aspects of the illustrated suturing technique using needles and suture attached to ferrules of instrument 10 may be similar to that shown in U.S. Pat. Nos. 5,431,666; 5,766,183; 6,997,931 B2; 7,731,727 B2 and European Patent No. EP 0669101, filed Feb. 23, 1995 and granted Oct. 14, 1998, which are incorporated by reference herein and used in the SEW-RIGHT® SR●5® and Running Device® and ESD™ products manufactured by LSI SOLUTIONS, Inc. (formerly LaserSurge, Inc.) of Victor, N.Y.

Figure 3:
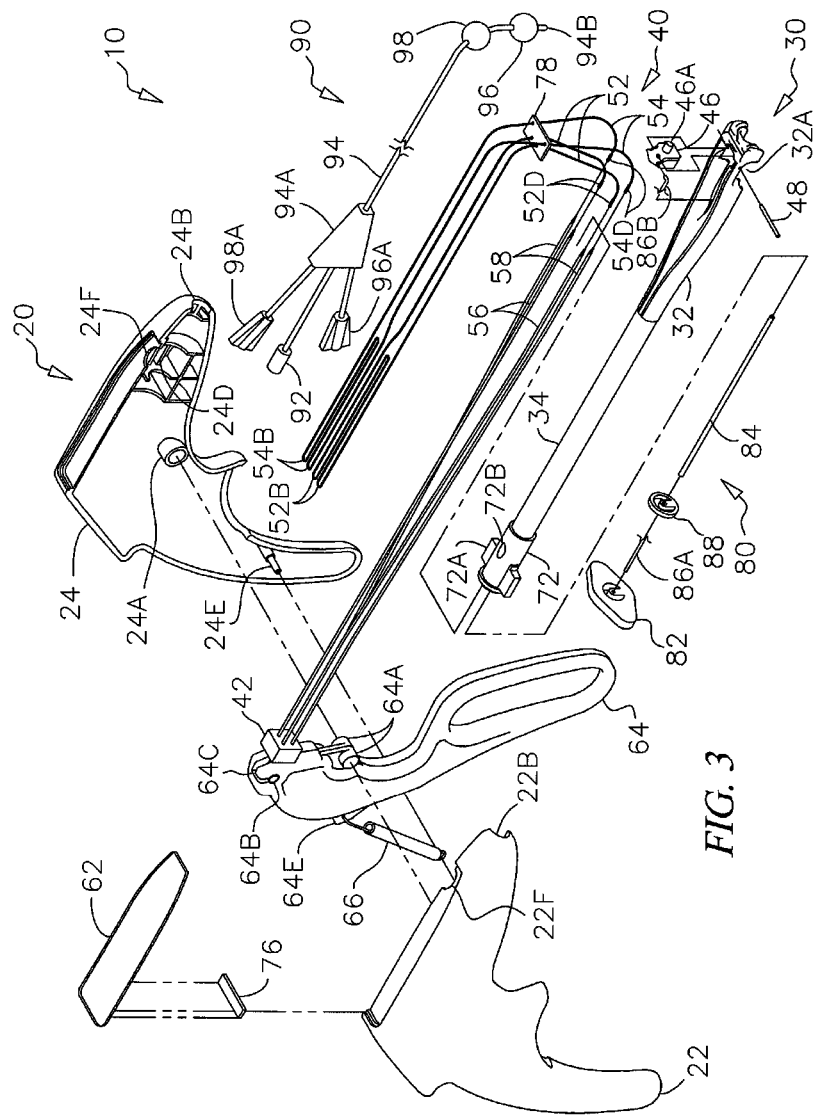
FIG. 3 is a partially exploded perspective view of the tissue suturing instrument of FIG. 1 in which the handle halves are separated and the functional components for suture placement, mechanical alignment and tissue engagement are highlighted.
Figure 4:
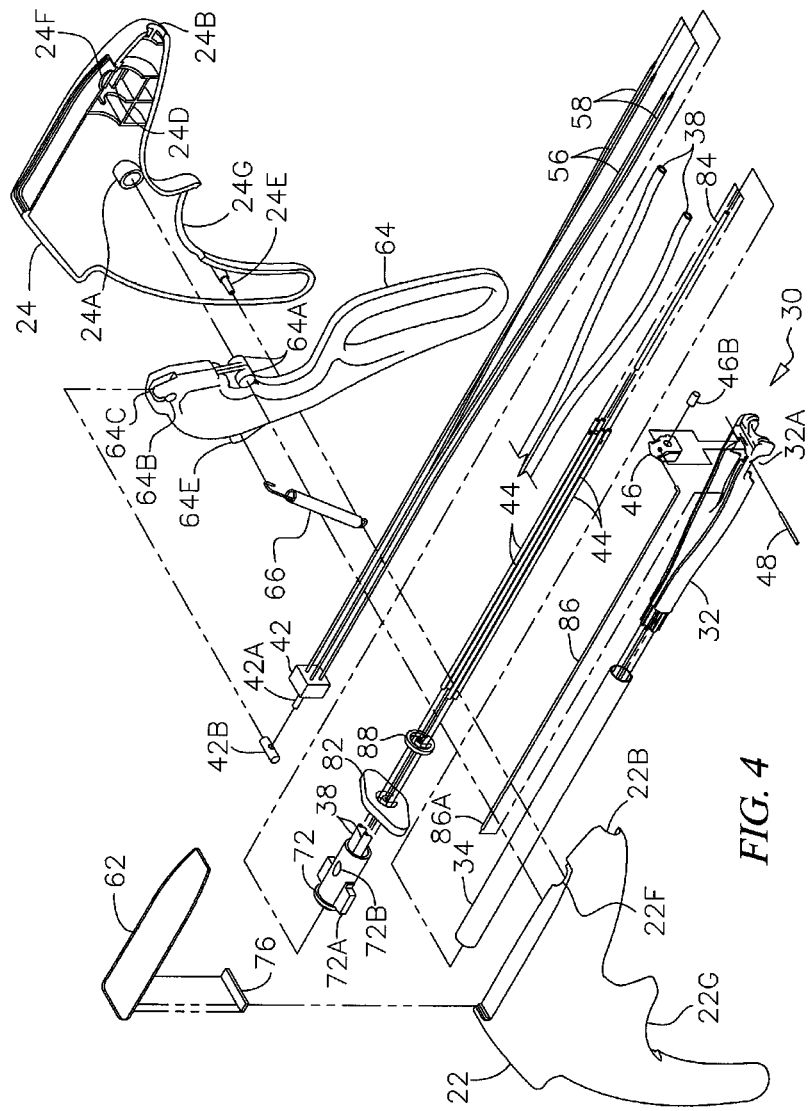
FIG. 4 is an exploded perspective view of the tissue suturing instrument of FIG. 1; except, to simplify this illustration for clarity, the suture and the tissue engagement assembly are omitted.

FIG. 2A is a perspective view of the tissue suturing instrument of FIG. 1 in which the right handle portion 22 of the housing of the instrument is removed to illustrate internal components. Note Section A-A of FIG. 2A is shown in cross section FIG. 2B. FIG. 3 is a partially exploded perspective view of the tissue suturing instrument of FIG. 1 in which the handle halves are separated highlighting the functional components for needle delivery, pledgeted concentric double mattress suture placement, rotating mechanical tissue alignment and a balloon assembly for enhancing tissue engagement. FIG. 4 is an exploded perspective view of the tissue suturing instrument of FIG. 1.

A lever 64 configured to be operated by the fingers of a user while grasping handle 20 provides for the extension and retraction of inner needles 56 and outer needles 58 of the instrument 10. Distally, an elongated shaft tube 34, shown here as rigid, but which may also be flexible, protrudes from the handle assembly 20. The housing of the handle assembly 20 has a body shaped like a pistol having a handle portion made of a two-piece construction of molded plastic components right handle 22 and left handle 24. Two pairs of elongated inner and outer needles 56 and 58, which may be made of metal, such as surgical stainless steel, extend from housing 20 through the shaft tube 34 into the tissue engaging distal end 32. Each of the inner and outer needles 56 and 58 has a non-tissue engaging end, the proximal attachment ends 56A and 58A, in the housing that are attached by gluing, welding, brazing or other such means into four corresponding holes in a needle attachment fixture 42. This needle attachment fixture 42 is fixed to a rotatable axle 42B using a slender connector shaft 42A.

The suturing instrument 10 includes an actuator member 64 preferably including a lever having two lever pins 64A extending into holes 22A and 24A in the sides of housing right and left handles 22 and 24 respectively, upon which pins the actuator member is pivotally mounted in the housing. A portion of the actuator lever 64 (FIGS. 3 and 4) extends through lever openings 22G and 24G (FIG. 4) in housing 20 to enable pivotal movement about pins 64A. An extension spring 66 is provided which hooks at one end in a spring attachment notch 64E of actuator lever 64 and is connected at the other end around a handle spring post 24E, which extends into a handle post receiving pocket located in the side of housing right and left handles 22 and 24 respectively, such that the actuator lever 64 is spring biased to retain actuator lever 64 normally in a forward position, as shown for example in FIG. 1. FIG. 3 illustrates the balloon tissue engaging assembly 90, which provides a common balloon tube 94 attached to a common hub 94a which communicates approximately with three ports; namely the guide wire port 92, the internal balloon port 96A and the external balloon port 98A. Internal balloon 96 and external balloon 94 are attached to common balloon tube 94 proximal to its distal open end 94B.

A slotted axle receiver 64B is formed in the actuator lever 64 and is shaped to receive the axle 42B of the needle attachment fixture 42 and its connector shaft 42A. The inner and outer needles 56 and 58 are driven forward by an operator pulling actuator lever 64 to pivot on lever pin axle 64A of actuator lever 64 within lever openings 22G and 24G. Shaft slot 64C (FIG. 3) is provided for connector shaft 42A to allow connection and rotation of the needle attachment fixture 42 about its axle 42B. While the lever illustrated is presently preferred, other mechanisms, such as a linear push-pull knob, a trigger or buttons, may be used.

With its right handle half 22 shown removed and its left handle half 24 shown in place, FIG. 2A best illustrates the relationship between the handle housing 20 and the elongated shaft tube 34. Note the winged shaft connector 72 nested in left handle 24 with its wing 72A on the right exposed along with its suture hole 72B. The unexposed left shaft connector wing engages in a corresponding connector wing opening 24D in left handle 24, which is best seen in FIG. 4. The winged shaft connector 72 may be attached to the elongated shaft tube 34 by glue, fasteners or other such means. To hold the shaft 34 within the handle 20, the protruding wings 72A of the shaft connector 72 engage the corresponding openings 22D (not shown) and 24D of handles 22 and 24. At its interface with handle assembly 20, elongated shaft tube 34 exits through shaft openings 22B and 24B. Also contained therein, as shown in FIG. 2B, are the inner needles 56 and outer needles 58, suture storage tubes 38 with inner suture 52 and outer suture 54, along with lock control tube 84 and lock control wire 86. Suture passes through suture passage openings 22F and 24F and handles 22 and 24, respectively.

The partially exploded perspective view of FIG. 3 highlights the major functional elements of the tissue suturing instrument 10, which include the handle assembly 20, a shaft tube assembly 30, a needle drive and suture, pledget storage assembly 40, a rotating mechanical alignment guide assembly 80, and a balloon tissue engaging assembly 90, which enable, respectively, pledgeted suture placement, more automated tissue alignment guidance and enhanced tissue engagement, all oriented over a guide wire placed through the targeted tissue. A clear plastic suture viewing window 62 revealing a compressive suture pad 76 gently holding the proximal tell-tale suture indicator loops 52B and 54B is shown in position relative to handle 20.

FIG. 4 is a fully exploded, perspective view of the tissue suturing instrument 10 showing its right handle 22, left handle 24, needle actuating lever 64 and its extension spring 66; however, the suture and balloon tissue engagement assembly are removed from this drawing for illustration clarity. The disassembled shaft tube assembly 30 comprises, from distal to proximal ends, a distal end 32, an elongated shaft tube 34, four needle guide tubes 44, a lock control tube 84 and two suture tubes 38. The lock control wire 86 is connected at its proximal end 86A to the sliding lock control knob 82 and bent at its distal end to engage the cam track 46A of the rotating mechanical tissue alignment guide 46.

Figure 5:
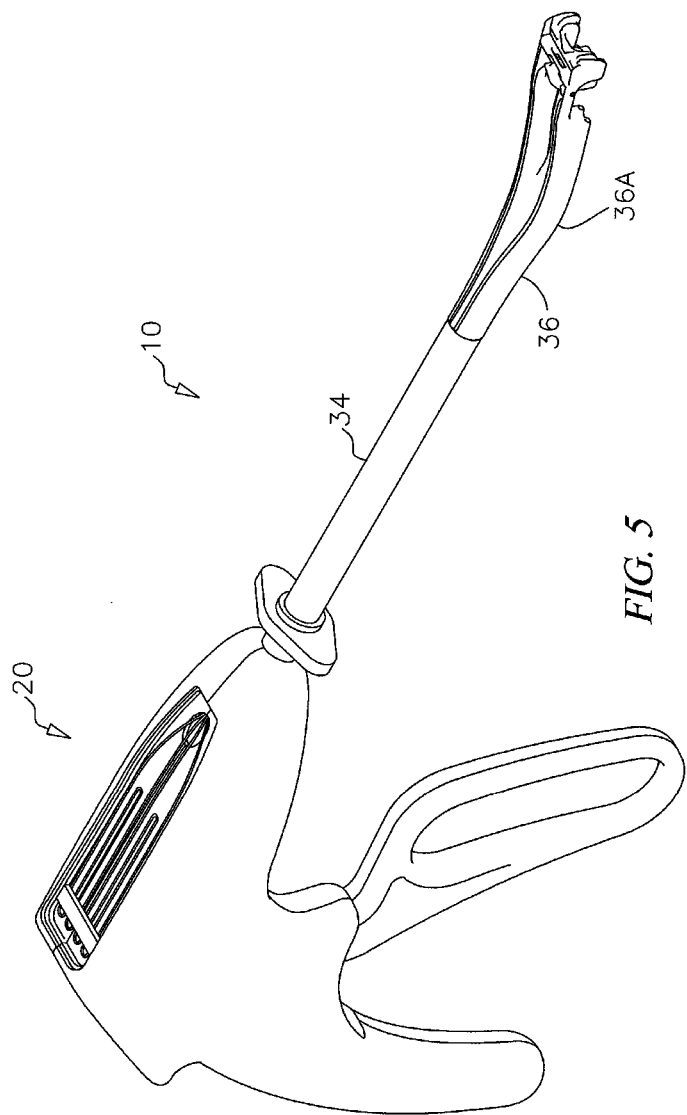
FIG. 5 is a perspective view of the tissue suturing instrument of FIG. 1 showing a curved distal end of the instrument.

FIG. 5 is a perspective view of the instrument 10 similar to FIG. 1 now shown having an elongated shaft tube 34 and an alternative distal end 36 that is bent, flexible, malleable or steerable as indicated at the bent section 36A. A non-straight or non-rigid shaft enables access to many potentially clinically relevant sites that are not reachable by straight or rigid instruments.

A primary function of this embodiment of the invention is to enable the accurate placement of two pledgeted horizontal mattress sutures at controlled depths in thick tissue; the individual components for this critical function are best seen isolated in FIG. 6A through FIG. 8D. A horizontal mattress suture, sometimes alternatively called a U-stitch, is created by enclosing a tissue location with a single stitch.

Now referring to FIGS. 6A-6D, the presently preferred embodiment of the invention uses two pairs of inner and outer needles 56 and 58 passing through an opening or welting trough 32A in a tissue receiving jaw in the distal end 32. Tissue appropriately held in this trough would receive four tissue bites and could thus accommodate two bites each for the two (or more) mattress sutures. Bite depths depend on location of the passing needle relative to the top of the tissue welt and to the tissue compression within the jaw. For example, for closure of the apex in the heart, one preferred device configuration has two inner needles 56 traveling 9.0 mm apart at a tissue depth of 4.0 mm across a tissue span of 9.5 mm. The two outer needles 58 are 13.2 mm apart from each other (2.1 mm apart from the adjacent corresponding inner needles) and pass at a tissue depth of 5 mm across 13.1 mm of tissue.

The distal ends of both sets of needles 56B and 58B engage and pick up both ends of the sutures by engaging their corresponding ferrules 52D and 54D (FIGS. 7A and 7B). Once the needles pass completely through the tissue and are fully advanced into the ferrules, the ferrules with their attached sutures are now secured to the needles, so that the retraction of the inner and outer needles 56 and 58 back through the tissue also pulls the inner and outer sutures 52 and 54 back through the tissue at the targeted site.

The needle advancement and retraction drive mechanism is isolated in FIGS. 6A-6D. The two inner needles 56 are shown here attached to the top two holes of the needle attachment fixture 42 at the proximal attachment ends 56A of the needles. The inner needle distal ends 56B lie between the outer distal ends 58B of the two outer needles 58. Outer needles 58 connect to the two lower holes of the needle attachment fixture 42 at their proximal attachment ends 58A. Force or squeezing on the lower half of the lever 64 directed toward the handle causes rotation about the lever pins, axle 64A. Forward pressure on the needle attachment fixture axle 42B by the slotted axle receiver 64B is translated by connector shaft 42A to drive the needle attachment fixture 42 forward along with the top of lever 64 upon lever squeezing. The needle attachment fixture 42 attached by its shaft 42A to its axle 42B can maintain a substantially horizontal orientation while being driven forward by rotating in the slotted axle receiver 64B of lever 64.

Release of lever 64 causes counter rotation about lever pins, axle 64A augmented by extension spring 66. Needle attachment fixture 42 then pulls its connected inner and outer needles 56 and 58 (along with their ferrules and sutures) back to the initial starting retracted position.

The needles are constrained within the elongated shaft tube 34 and the distal end 32 of the instrument so that translational forces extended on the proximal needle attachment fixture 42 cause the distal ends 56B and 58B of the inner and outer needles 56 and 58 to advance from their proximal retracted position across the tissue receiving jaw and through any tissue held within this trough. The distal ends 56B and 58B enter into the ferrules 52D and 54D (shown in FIGS. 7A and 7B) held in their ferrule compartments 32B (shown in FIGS. 8B and 8D) on the distal side of the tissue engaging jaw or welting trough 32A.

FIG. 7A highlights the suture storage capacity of this preferred embodiment. Note, for the purpose of clearer illustration, all four ferrules 52D and 54D are shown outside of their ferrule compartments 32B (where they would actually be located prior to pick up). The suture pad 76 held between the clear suture viewing window 62 and the space in the top of handle 20 holds suture indicator loops 52B and 54B in place by mild compression. The suture pad 76 holds the suture indicator loops 52B and 54B while maintaining tension on the suture segments to keep the distal ferrules 52D and 54D securely in place in their ferrule compartments. Movement or shortening of suture indicator loops 52B and 54B is seen through window 62 thereby indicating needle retraction, successful ferrule pick up and that the corresponding sutures 52 and 54 have been pulled through the tissue engaging jaw 32A. The elongated shaft tube break-out segment of FIG. 7A, shows the suture storage tubes 38 along with inner and outer sutures 52 and 54. The inner and outer sutures 52 and 54 again are shown in the suture passage hole 72B of the winged shaft connector 72.

FIG. 8A illustrates a partial top view of the device showing the indicator loops 52B and 54B held by the suture pad 76 beneath the clear suture window 62. Note all four suture loops 52B and 54B are on the proximal side of the suture pad 76 indicating the ferrules are in their compartments. FIG. 8B is a partial end view of the distal end of the instrument of FIG. 8A. This view shows all four ferrules 52D and 54D still held within their ferrule compartments 32B.

FIG. 8C shows the altered, more distal location of the suture indicator loops 52B and 54B relative to the suture pad 76 indicating that the suture has now passed through the tissue engaging jaw 32A in the distal end 32. By pulling the ferrules 52D and 54D, the distal ends of each inner and outer sutures 52 and 54 pass through the tissue engaging jaw 32A, and the indicator loops 52B and 54B of the corresponding sutures are moved distally in the same direction as the movement of the sutures through the elongated shaft tube 34. FIG. 8D shows four segments of inner and outer sutures 52 and 54 now spanning the welting trough in the jaw 32A of the distal end 32.

FIGS. 9A-10B and FIGS. 11A-13B next address the components of the mechanical tissue alignment guide and the tissue engagement assemblies, respectively.

FIGS. 9A and 9B illustrate the pivotal mechanical alignment guide of the instrument of FIG. 1. Note that the right side of the distal end 32 has been removed to better reveal the functional components of this tissue alignment mechanism. This novel alignment guide integrated into this device permits the aligned passage of the instrument over a pre-placed temporary guide wire centered in the protruding guide nipple 46B (shown separated from 46 in FIG. 4) of the rotating mechanical tissue alignment guide 46. This rotation is important because the end of the device 10 may need to traverse a narrow access channel, such as the space between non-retracted ribs. With a rotating alignment guide in the end 32 of this device, the guide wire within the mechanical alignment guide can pass longitudinally through narrow openings in the body; if the mechanical alignment guide did not rotate and was held in the up, perpendicular orientation, the guide wire would also be held perpendicular (normal or 90 degrees) relative to the long access of the shaft, necessitating a larger access opening.

Figure 10A:
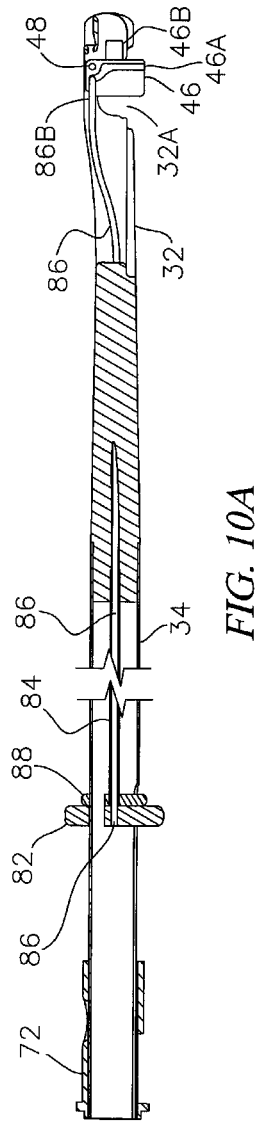
FIG. 10A shows a cross-sectional view of the unlocked mechanical alignment guide.
Figure 10B:
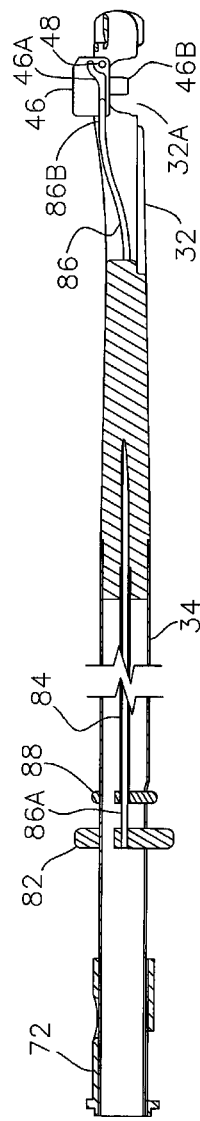
FIG. 10B shows a cross-sectional view of the locked mechanical alignment guide.

In FIGS. 9A-9B, the elongated body shaft tube 34 (shown shortened) connects the distal end 32 to the handle 20 (not shown) via the winged shaft connector 72. Connected to the elongated shaft tube 34 is the proximal lock control tube holder fixture 88, which fixes the proximal end of the lock control tube 84 inside of the elongated shaft tube 34 and is best shown in FIGS. 10A and 10B. The sliding lock control knob 82 slides toward the handle, which is here represented by the winged shaft connector 72. The sliding lock control knob 82 is connected to the lock control wire 86 at the lock control wire proximal end 86A; also best seen in FIGS. 10A and 10B. By moving the sliding lock control knob 82 and its attached lock control wire 86 toward the handle, the lock control wire moves away from the proximal lock control tube holder 88 and its connected lock control tube 84. A passageway exists in the distal end 32 for the lock control wire 86 which has a distal bent end 86B that engages a cam track 46A integrated into the rotating mechanical tissue alignment guide 46. When unlocked, the rotating mechanical tissue alignment guide 46 partially rotates about its axle 48.

FIG. 9B illustrates the same features as FIG. 9A except now the sliding lock control knob 82 is moved proximally, pulling its attached lock control wire 86 also proximally thereby causing the rotating mechanical tissue alignment guide 46 to rotate and lock in place with the lock control wire distal bent end 86B engaging the straight part of the cam track 46A.

FIGS. 10A and 10B are the cross-sectional views corresponding to FIGS. 9A and 9B; these views better illustrate the mechanism in which the sliding lock control knob 82 attached to the lock control wire 86 moves relative to the proximal lock control tube holder 88 and the lock control tube 84. In FIG. 10A, the mechanical tissue alignment guide 46 is shown rotated down in the unlocked position with the integrated protruding nipple 46B facing forward. As best seen in FIG. 10A, the distal bent end 86B runs in a curved portion of the cam track or radially about the rotating alignment guide axle 48 so that the mechanical tissue alignment guide 46 moves freely when the lock control wire distal bent end 86B is in the forward unlocked position. In FIG. 10B, with the distal bent end of the lock control wire 86B now pulled back by moving the sliding lock control knob 82 toward the handle, the rotating mechanical tissue alignment guide 46 is fixed in the up position with its integrated protruding nipple 46B oriented facing down, perpendicular to the long axis of the distal end 32 and generally centered within the tissue receiving jaw or welting trough 32B and pointing directly towards the surface of the targeted tissue (not shown).

FIGS. 11A-12C show the components of a preferred embodiment of a balloon-based tissue engaging and compressing assembly of this device. FIGS. 13A and 13B show an alternative tissue engagement assembly providing an internal expanding hinged frame and an external compression spring. Either tissue engagement assembly of this invention allows the tissue to be compressed within the tissue engaging jaw 32A of the device using mechanical forces applied to the tissue to form a welt and better enable needle passage. This mechanical tissue engagement approach permits the distal end to form a welt and hold tissue even if the end of the device cannot be pushed down upon that tissue due to its remote location.

FIG. 11A shows the distal end 32 attached to the end of the elongated shaft tube 34. In FIGS. 11A-11C, the right side of the distal jaw is partially removed to better illustrate functionality. The rotating mechanical tissue alignment guide 46 is shown locked into the up and perpendicular position. A common balloon tube 94 with both balloons not expanded is shown passing parallel along the elongated shaft tube 34, along the distal end 32 of this device and passing through the downward facing integrated protruding nipple 46B of the rotating mechanical tissue alignment guide 46. This common balloon tube 94 follows over an existing guide wire (not shown), which will be further addressed starting in FIGS. 15A-15H.

FIG. 11B shows the same features as FIG. 11A except now the internal balloon 96 is expanded on the distal side of the rotating mechanical tissue alignment guide 46; when in actual use, internal balloon 96 would be positioned internal to the targeted tissue.

FIG. 11C shows the same features as FIG. 11B, but now the external balloon 98 is expanded to draw the internal balloon feature 96 back toward the distal end 32. By inflating both the internal 96 and external 98 balloons, the jaw welt forming trough 32A is sandwiched on top of the targeted tissue between the balloons.

Figures 12A, 12B, 12C:
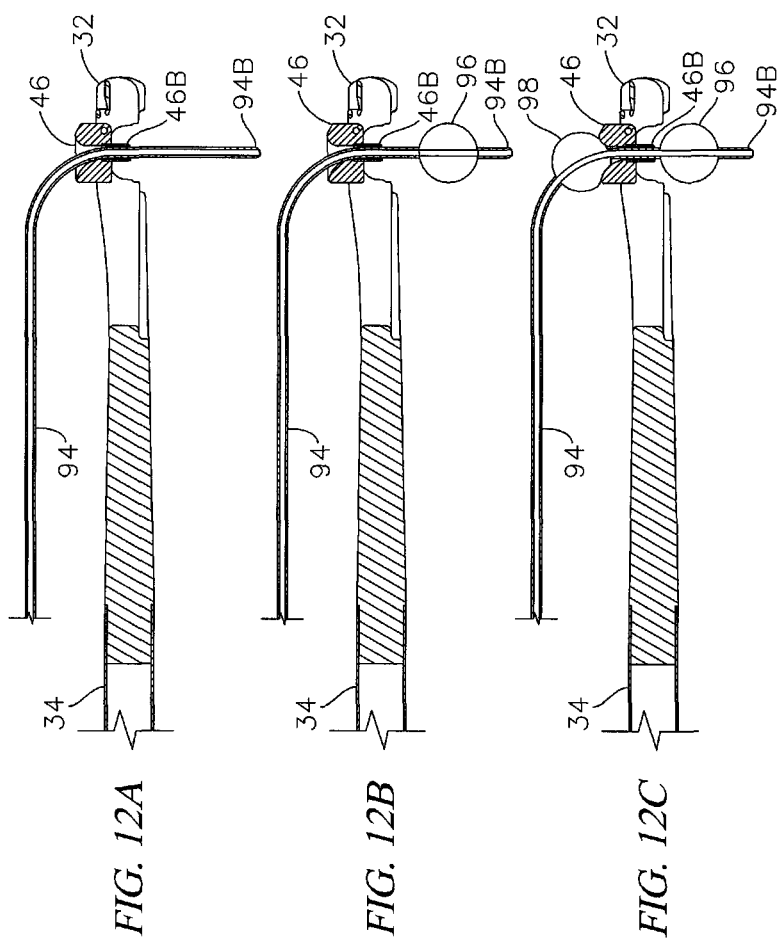
FIG. 12A shows a section view of FIG. 11A.
FIG. 12B shows a section view of FIG. 11B.
FIG. 12C shows a section view of FIG. 11C.

FIGS. 12A-12C are cross sections corresponding to the previous drawings. These illustrations highlight the relative location of the common balloon tube 94 and its distal end 94B. They show the elongated shaft tube 34 relative to the distal end 32 and the common balloon tube 94 passing through the now downward oriented integrated protruding nipple 46B of the rotating mechanical tissue alignment guide 46 in the up and locked position.

FIG. 12A shows the common balloon tube 94 with both balloons not expanded. FIG. 12B shows the same as FIG. 12A except now the internal balloon is expanded. FIG. 12C shows the same as FIG. 12B except now the external balloon 98 is also expanded. The expansion of the external balloon 98 draws the internal balloon 96 and the common balloon tube distal opening 94B back up towards the jaw. When the tissue is sandwiched between the two balloons 96 and 98 and the welting trough 32A of the distal end 32, the tissue is compressed in the desired location for forming a welt and ensuring adequate tissue bites for suturing.

FIGS. 13A and 13B provide a perspective view and a cross-sectional view, respectively, of an alternative tissue engagement mechanism assembly embodiment. FIG. 13A shows the elongated shaft tube 34 attached to distal end 32 with its right side segment partially removed for illustration. The mechanical alignment guide 46 is in the up and locked position with its integrated protruding nipple 46B facing the tissue site. Now, however, instead of having a balloon internal tissue engagement means, an internal hinged frame mechanical expander anchor 102 is provided in this embodiment. The expander anchor 102 shown here is a slit tube with living hinges which when under compression expands radially outward. Tension in the proximal direction on the push-pull conduit internal mechanical expander 102A of the expander anchor 102 causes shortening of this hinged frame mechanism, so that the hinged frame segments expand outwardly creating an internal anchor 102. The push-pull conduit 102A traverses through another conduit, the internal hinged frame mechanical expander conduit 102B, which travels inside of the external compression spring tube 104A. That spring tube 104A is connected to an external compression spring 104. By pulling on the push-pull conduit internal mechanical expander 102A and holding the conduit 102B, the internal hinged frame mechanical expander anchor 102 opens and draws the tissue up into the welting jaw. By pushing on the external compression spring tube 104A, the external compression spring 104 pushes distally out on the exposed top of the alignment guide 46 of distal end 32 so tissue is pushed and pulled into the tissue receiving trough 32A.

Next the features of the present invention will be shown together to illustrate the coordination of suturing, alignment and engagement component functionality. For clarity, FIGS. 14A-14G will not include an element to represent a segment of tissue.

FIG. 14 shows a partial perspective view of the handle and a more blown up distal end view of the instrument of FIG. 1. This series of drawings utilizes the common balloon tube 94 mediated assembly embodiment as a tissue engagement assembly. Handle 20 is shown with a suture viewing window 62 and suture pad 76. In FIG. 14A, the sliding lock control knob 82 is shown in the unlocked position. Lever 64 is shown in its forward position. The common balloon tube 94 is shown coursing through the tissue alignment guide 46 of the distal end 32, the mechanical alignment guide 46 is pointed with its nipple 46B (not seen in this view) directed generally forward along the long axis of the instrument end. The common balloon tube 94 is shown going through the mechanical alignment guide 46 with its distal open end 94B now outside of the device. Inner and outer sutures 52 and 54 are shown in their loading position along with a four-holed pledget 78.

FIG. 14B is much like FIG. 14A except now the sliding lock control knob 82 is pulled back and the rotating mechanical tissue alignment guide 46 has been rotated up and locked so that the protruding guide tube (not seen) projects downward towards and perpendicular to the tissue surface. The common balloon tube 94 is now oriented generally perpendicular to the jaw, where it is most useful in wound site alignment for pulling the tissue directly into welting trough 32A. FIGS. 14A and 14B best illustrate so far why a rotatable alignment guide provides better access through narrow spaces; the vertical profile at the distal end 32 is much lower in the configuration shown in FIG. 14A than it is in the configuration shown in FIG. 14B. In FIG. 14A, the orientation of common balloon tube 94 within the distal end 32 can be appreciated to permit longitudinal passage through a narrow space. Whereas in FIG. 14B, with the rotating mechanical tissue alignment locking guide 46 now locked in its up position, the vertical height necessary to pass this instrument over a perpendicular oriented guide wire through a narrow space (such as between ribs) would be much greater.

FIG. 14C follows FIG. 14B but now shows both the internal balloon 96 and the external balloon 98 expanded. The actual sequence of use of this device would have the internal balloon filled first, and the external balloon filled next, to optimize compression of the device onto the tissue. The rotating mechanical tissue alignment guide 46 is locked up and the other elements are in their loaded positions.

FIG. 14D now illustrates that lever 64 is partially squeezed and the needle tips 56B and 58B are partially entering the tissue receiving jaw space 32A. If tissue was in the jaw's welting trough 32A, these needles would penetrate that tissue.

FIG. 14E shows the same configuration and function as 14D except now the needles have traveled fully forward, entered the ferrules held in the ferrule compartments and have been pulled back along with their attached sutures through the jaw. FIG. 14E shows inner and outer sutures 52 and 54 traversing the trough 32A, after being pulled back with their attached ferrules on their retracted needles. In actual use, the needles, ferrules and sutures would pass through a welt formed in the tissue.

FIG. 14F shows the same of configuration as FIG. 14E except now the external balloon has been unexpanded and the sliding lock control knob 82 has been pushed back forward thereby releasing the rotating mechanical tissue guide 46 so that it can now swing freely. In 14F, the distal end 32 of the device can be pulled away from the targeted tissue site and the still expanded internal balloon. FIGS. 14E and 14F show the suture indicator loops 52B and 54B are now distal to the suture pad 76.

Figure 14G:
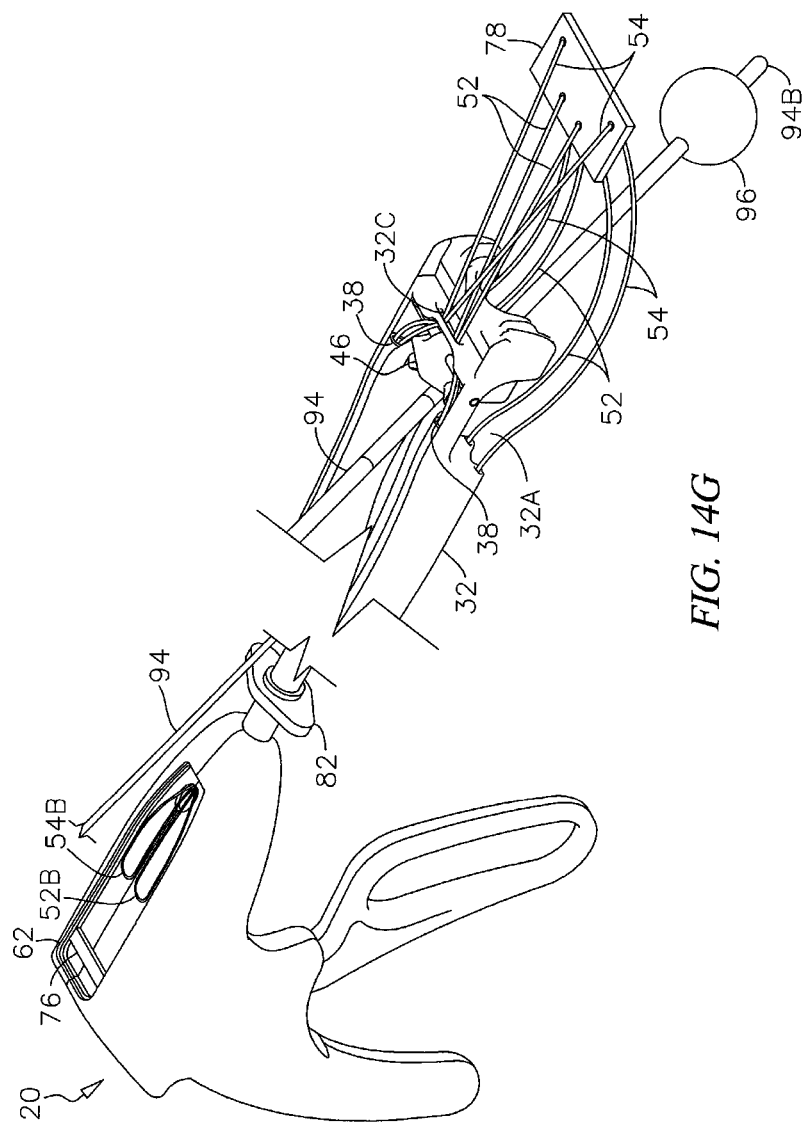
FIG. 14G shows a partial perspective view presenting the instrument's distal end with the alignment mechanism unlocked with the inner tissue engagement balloon still expanded, the outer tissue engagement balloon not expanded while the suture is shown now paying out and the pledget is displaced from its loaded position.

The final illustration of this functional series demonstration, FIG. 14G, shows even a larger view of the distal end 32. The suture indicator loops 52B and 54B indicate even further payout of the suture. While the internal balloon 96 is still up, the device distal end 32 is pulled away from the proposed wound site leaving the four suture bites in place and permitting the four-holed pledget 78 to release from its loaded position at the far end of the device distal end 32. The suture passage slot 32C is well seen here in the distal end 32 with four suture segments passing through it along with both integrated suture storage tubes 38.

FIGS. 15A-H are similar in their contents to the last series, FIGS. 14A-14G, except in these illustrations a guide wire 122 is shown going through a planar tissue sample segment 124.

FIG. 15A shows the distal end 32 advancing with the common balloon tube 94 passing through the unlocked rotating mechanical tissue alignment guide 46, passing over a guide wire 122, toward a planar tissue sample 124 which is also traversed by the guide wire 122. Sutures and needles are in their loaded pre-activated position.

FIG. 15B shows the instrument of FIG. 15A now with its rotating mechanical tissue alignment guide 46 locked in the upright position, the nipple entering the wound site, the common balloon tube 94 passing through a planar tissue sample structure 124, and the internal balloon 96 inflated.

FIG. 15C shows the next step in which the external balloon 98 is now inflated. With both the internal and external balloons 96 and 98 inflated, the planar tissue sample 124 conforms to a zone of tissue compression 124A to form a welt through mechanical engagement with the welting trough 32A and the internal balloon 96.

FIG. 15D illustrates with hidden lines how the inner and outer needles 56 and 58 could pass through the welted zone of tissue compression 124A now engaged in the welting trough of the jaw. FIG. 15E illustrates with hidden lines, the needles are now retracted back and sutures 52 and 54 are traversing the four suture bites in the targeted tissue.

FIG. 15F illustrates the distal end 32 with the rotating mechanical tissue alignment guide 46 unlocked, the external balloon 98 down, the internal balloon 96 still inflated and inside of the planar tissue sample 124 to illustrate how sutures 52 and 54 would traverse from the pledget 78 around the common balloon tube 94 and out on the opposite side of the planar tissue segment 124 now without a zone of tissue compression over a guide wire 122. The pledget 78 has been lifted away from the planar tissue sample 124 to illustrate how the suture 52 and 54 would traverse from the pledget 78 around the common balloon tube 94 and out on the opposite side.

FIG. 15G now completes the removal of the distal end that was shown in FIG. 15F. Four segments of sutures 52 and 54 are placed now in configuration around the guide wire and the balloon. Not shown here is the therapeutic intervention step to provide cannula or instrument access between the placed horizontal mattress sutures as would be needed in a therapeutic procedure. In a heart apical access procedure, for example, a cannula must be placed over the guide wire into the heart. The internal balloon 96 would be deflated and the common balloon tube 94 would be removed leaving the guide wire 122 still in place in the heart. To ensure hemostasis, tension can be placed on the sutures exiting the tissue to temporarily tighten the mattress suture configuration. A dilator or balloon assembly could be passed over the indwelling guide wire to expand the hole between the mattress sutures to enable cannula placement access for a therapeutic intervention.

FIG. 15H now shows the tightened closure of the horizontal mattress sutures provided in the previous steps. Surgical hand tied or mechanical suture knots 132 can be placed to complete the closure of each horizontal mattress suture. The curved line 1248 at the wound closure site between the pledgets represents the subsequently closed dilated access site that has now been secured between the two horizontal mattress sutures.

FIG. 16A illustrates the thorax 140 of an elderly man. The rib structure is highlighted to reveal the location of the space between the ribs and the underlying heart 152. The front or anterior surface of the heart's apex projects towards the patient's left lateral chest wall, below the nipple 146, where, for example, access to the apex of the heart is enabled through the left lateral approach. The interspaces 144 below the $5^{th}$ and $6^{th}$ ribs 142 provide a more direct access route. Access to the ascending aorta can be through a right upper lateral approach.

FIG. 16B illustrates cardiac anatomy in the thorax 140 without ribs to obscure viewing the underlying structures. The apex 152A of the left ventricle of the heart 152 lies in the left lateral direction. The anterior ascending aorta 154, a potential access site for a cardio-pulmonary bypass cannulation, is shown central in the mid chest.

FIG. 17A shows a guide wire 122 placed in the apex 152A of the left ventricle. The region typically is somewhat devoid of fat and is often called the left ventricular "bald spot." Placing a guide wire through the heart into the chamber enables the subsequent placement of an access tube into the chamber for minimally invasive heart interventions. In FIG. 17B, the device end 32 shown placed over the guide wire, but prior to external balloon expansion on the common balloon tube 94, is oriented so the elongated shaft tube 34 would pass through the left lateral chest wall. FIG. 17C shows the completed wound closure site at the end of the transapical procedure. The initial pledget 78 along with the inner suture pledget 126 and outer suture pledget 128 surround the closed access site.

FIGS. 18A-18C are similar to FIGS. 17A-17C described in the previous series. FIG. 18A, however, shows a guide wire now placed in the anterior surface of the anterior ascending aorta 154. This tubular structure, the body's largest artery, is a frequent place for cannulation for procedures requiring cardio-pulmonary bypass. With the distal end 32 of the device as shown in position over the guide wire 122 in FIG. 18B, the elongated shaft tube 34 of this instrument would pass through the right lateral chest wall. The common balloon tube 94 is again shown in place with its external balloon not expanded. The final aortic wound site closure secured with pledgets 78, 126 and 128 and horizontal mattress sutures 52 and 54 is shown in FIG. 18C.

While the invention has been described in connection with a number of presently preferred embodiments thereof, those skilled in the art will recognize that many modifications and changes may be made therein without departing from the true spirit and scope of the invention which accordingly is intended to be defined solely by the appended claims.

The invention claimed is:

1. A device for placing one or more sutures through a section of tissue, the device comprising:
   a tissue welting trough;
   an alignment guide pivotable in relation to the tissue welting trough and defining an opening configured to allow a guide wire to be passed there through;
   at least one pair of retractable needles extendable through the tissue welting trough and configured to be able to pass through at least two portions of a tissue section when such a tissue section is present in the tissue welting trough; and an expandable tissue engaging member selectively expandable from a collapsed configuration passable through the opening defined by the alignment guide to an expanded configuration large enough to engage a tissue section and urge it into the tissue welting trough and form a welt in the tissue section.

2. The device of claim 1, wherein the alignment guide further comprises a nipple extending from the opening into the tissue welting trough.

3. The device of claim 1, further comprising a lock control coupled to the alignment guide and configured to selectively set the alignment guide in an unlocked position or a locked position.

4. The device of claim 3, wherein the alignment guide resists pivoting in relation to the tissue welting trough when the alignment guide is in the locked position.

5. The device of claim 4, wherein:
   the alignment guide further comprises a nipple extending from the opening into the tissue welting trough; and
   the nipple is generally aligned with and centered in the tissue welting trough when the alignment guide is in the locked position.

6. The device of claim 4, wherein:
   the device further comprises a shaft having a distal end coupled to the tissue welting trough;
   the alignment guide further comprises a nipple extending from the opening into the tissue welting trough; and
   the nipple is substantially orthogonal to a longitudinal axis of the shaft when the alignment guide is in the locked position.

7. The device of claim 3, further comprising:
   a shaft having a distal end coupled to the tissue welting trough; and
   a lock control knob towards a proximal end of the lock control, the lock control knob moving with respect to the shaft.

8. The device of claim 1, wherein:
   the at least one pair of retractable needles are extendable through the tissue welting trough and configured to be able to pass through at least two portions of a tissue section, when such a tissue section is present in the tissue welting trough, such that the full thickness of the tissue is not penetrated.

9. The device of claim 8, further comprising:
   at least one pair of ferrule receiving compartments opening into the tissue welting trough.

10. The device of claim 9, further comprising:
    at least one suture having a ferrule at each end, each of the ferrules being disposed in one of the ferrule receiving compartments.

11. The device of claim 9, wherein:
    the at least one pair of ferrule receiving compartments comprises two pairs of ferrule receiving compartments opening into the tissue welting trough; and
    the device further comprises two sutures, each suture having a ferrule at each end, each of the ferrules being disposed in one of the ferrule receiving compartments.

12. The device of claim 11, wherein the ferrule receiving compartments are arranged in a trapezoidal configuration.

13. The device of claim 9, further comprising a pledget threaded on the at least one suture.

14. The device of claim 13, further comprising a suture pad maintaining tension on the sutures.

15. The device of claim 13, further comprising a window through which the sutures can be seen.

16. The device of claim 1, wherein each of the needles in the at least one pair of retractable needles is extendable through the tissue welting trough at substantially the same time.

17. The device of claim 1, wherein each of the needles in the at least one pair of retractable needles is extendable through the tissue welting trough on substantially parallel paths.

18. The device of claim 1, wherein:
    the at least one pair of retractable needles comprises a plurality of pairs of retractable needles extendable through the tissue welting trough; and
    each pair of the plurality of pairs of retractable needles is configured to be able to pass through at least two portions of a tissue section when such a tissue section is present in the tissue welting trough.

19. The device of claim 18, wherein each pair, of the plurality of pairs of retractable needles, is concentric.

20. The device of claim 18, wherein each pair, of the plurality of pairs of retractable needles, has a different needle spacing.

21. The device of claim 18, wherein each pair, of the plurality of pairs of retractable needles, has a different depth with reference to the tissue welting trough.

22. The device of claim 1, wherein the expandable tissue engaging member comprises an inflatable balloon.

23. The device of claim 1, wherein the expandable tissue engaging member comprises an internal expanding hinged frame and/or an external compression spring.

24. A device for placing one or more sutures through a section of tissue, the device comprising:
   a) a tissue welting trough;
   b) an alignment guide pivotable in relation to the tissue welting trough and defining an opening configured to allow a guide wire to be passed there through;
   c) a lock control coupled to the alignment guide and configured to selectively set the alignment guide in an unlocked position or a locked position, wherein the alignment guide resists pivoting in relation to the tissue welting trough when the alignment guide is in the locked position;
   d) a shaft having a distal end coupled to the tissue welting trough;
   e) a lock control knob towards a proximal end of the lock control, the lock control knob moving with respect to the shaft;
   f) at least one pair of retractable needles extendable through the tissue welting trough and configured to be able to pass through at least two portions of a tissue section when such a tissue section is present in the tissue welting trough;
   g) at least one pair of ferrule receiving compartments opening into the tissue welting trough;
   h) at least one suture having a ferrule at each end, each of the ferrules being disposed in one of the ferrule receiving compartments; and
   i) an expandable tissue engaging member selectively expandable from a collapsed configuration passable through the opening defined by the alignment guide to an expanded configuration large enough to engage a tissue section and urge it into the tissue welting trough and form a welt in the tissue section.

25. The device of claim 24, wherein:
   the alignment guide further comprises a nipple extending from the opening into the tissue welting trough; and
   the nipple is generally aligned with and centered in the tissue welting trough when the alignment guide is in the locked position.

26. The device of claim 24, wherein:
   the alignment guide further comprises a nipple extending from the opening into the tissue welting trough; and
   the nipple is substantially orthogonal to a longitudinal axis of the shaft when the alignment guide is in the locked position.

27. The device of claim 24, wherein each of the needles in the at least one pair of retractable needles is extendable through the tissue welting trough on substantially parallel paths.

28. A device for placing one or more sutures through a section of tissue, the device comprising:
   a) a tissue welting trough;
   b) an alignment guide pivotable in relation to the tissue welting trough and defining an opening configured to allow a guide wire to be passed there through;
   c) a lock control coupled to the alignment guide and configured to selectively set the alignment guide in an unlocked position or a locked position, wherein the alignment guide resists pivoting in relation to the tissue welting trough when the alignment guide is in the locked position;
   d) at least one pair of retractable needles extendable through the tissue welting trough and configured to be able to pass through at least two portions of a tissue section when such a tissue section is present in the tissue welting trough;
   e) at least one pair of ferrule receiving compartments opening into the tissue welting trough;
   f) at least one suture having a ferrule at each end, each of the ferrules being disposed in one of the ferrule receiving compartments; and
   g) an expandable tissue engaging member selectively expandable from a collapsed configuration passable through the opening defined by the alignment guide to an expanded configuration large enough to engage a tissue section and urge it into the tissue welting trough and form a welt in the tissue section.

29. The device of claim 28, wherein:
   the alignment guide further comprises a nipple extending from the opening into the tissue welting trough; and
   the nipple is generally aligned with and centered in the tissue welting trough when the alignment guide is in the locked position.

30. The device of claim 28, wherein:
   the device further comprises a shaft having a distal end coupled to the tissue welting trough;
   the alignment guide further comprises a nipple extending from the opening into the tissue welting trough; and
   the nipple is substantially orthogonal to a longitudinal axis of the shaft when the alignment guide is in the locked position.

31. The device of claim 28, wherein each of the needles in the at least one pair of retractable needles is extendable through the tissue welting trough on substantially parallel paths.

32. A device for placing one or more sutures through a section of tissue, the device comprising:
   a) a tissue welting trough;
   b) a shaft having a distal end coupled to the tissue welting trough;
   c) an alignment guide pivotable in relation to the tissue welting trough and defining an opening configured to allow a guide wire to be passed there through, and wherein the alignment guide further comprises a nipple extending from the opening into the tissue welting trough;
   d) a lock control coupled to the alignment guide and configured to selectively set the alignment guide in an unlocked position or a locked position, wherein:
      1) the alignment guide resists pivoting in relation to the tissue welting trough when the alignment guide is in the locked position; and
      2) the nipple is substantially orthogonal to a longitudinal axis of the shaft when the alignment guide is in the locked position;
   e) a lock control knob towards a proximal end of the lock control, the lock control knob moving with respect to the shaft;
   f) two pairs of retractable needles extendable through the tissue welting trough and configured to be able to pass through a tissue section when such a tissue section is present in the tissue welting trough;
   g) four ferrule receiving compartments opening into the tissue welting trough;
   h) two sutures, each having a ferrule at each end, each of the ferrules being disposed in one of the ferrule receiving compartments; and
   i) an expandable tissue engaging member selectively expandable from a collapsed configuration passable through the opening defined by the alignment guide to an expanded configuration large enough to engage a tissue section and urge it into the tissue welting trough and form a welt in the tissue section.

33. The device of claim 32, wherein each of the needles in the two pairs of retractable needles is extendable through the tissue welting trough on substantially parallel paths.

34. The device of claim 32, wherein each pair, of the two pairs of retractable needles, is concentric.

* * * * *